United States Patent
Suenaga et al.

(10) Patent No.: US 9,410,038 B2
(45) Date of Patent: Aug. 9, 2016

(54) COMPOUND, INK, INK CARTRIDGE AND INK JET RECORDING METHOD

(71) Applicant: CANON KABUSHIKI KAISHA, Tokyo (JP)

(72) Inventors: Masahiro Suenaga, Kawasaki (JP); Kaoru Takahashi, Saitama (JP); Yasuaki Murai, Kawasaki (JP); Takeshi Miyazaki, Ebina (JP); Yutaka Tani, Yokohama (JP); Masashi Hirose, Machida (JP); Ryosuke Nagao, Kawasaki (JP); Yoshio Kinoshita, Tokyo (JP); Yoshihide Aikawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 328 days.

(21) Appl. No.: 14/219,797

(22) Filed: Mar. 19, 2014

(65) Prior Publication Data

US 2014/0285567 A1    Sep. 25, 2014

(30) Foreign Application Priority Data

Mar. 21, 2013   (JP) .................................. 2013-057563

(51) Int. Cl.
| | | |
|---|---|---|
| *C09D 11/328* | (2014.01) | |
| *C09B 11/12* | (2006.01) | |
| *C09B 11/24* | (2006.01) | |
| *C07D 311/82* | (2006.01) | |
| *B41J 2/175* | (2006.01) | |

(52) U.S. Cl.
CPC ............. *C09B 11/12* (2013.01); *B41J 2/17503* (2013.01); *C07D 311/82* (2013.01); *C09B 11/24* (2013.01); *C09D 11/328* (2013.01)

(58) Field of Classification Search
CPC ...... C09D 11/328; C09B 11/12; C09B 11/24; C07D 311/82; B41J 2/17503
USPC ............. 106/31.43; 549/388, 394; 347/20, 86
See application file for complete search history.

(56) References Cited

U.S. PATENT DOCUMENTS

| | | | | |
|---|---|---|---|---|
| 7,083,667 B2* | 8/2006 | Murai | ................. | C09D 11/328 106/31.43 |
| 7,141,342 B2* | 11/2006 | Toyoda | ................ | G03G 9/0806 430/108.14 |
| 7,176,317 B2* | 2/2007 | Banning | .................. | C09B 11/12 546/196 |
| 8,343,269 B2* | 1/2013 | Takahashi | ............ | C09D 11/328 106/31.43 |
| 2011/0067598 A1* | 3/2011 | Takahashi | ............... | C09B 11/24 106/31.43 |
| 2014/0004458 A1* | 1/2014 | Tani | ........................ | C09B 11/24 430/108.21 |
| 2014/0005417 A1* | 1/2014 | Takahashi | ............ | C07D 311/82 549/394 |

FOREIGN PATENT DOCUMENTS

| | | |
|---|---|---|
| CN | 1576278 A | 2/2005 |
| CN | 102020866 A | 4/2011 |
| EP | 2302001 A1 | 3/2011 |
| GB | 1503380  * | 3/1978 |
| JP | 09/157562  * | 6/1997 |
| JP | H09-241553 A | 9/1997 |
| JP | 2008-094897 A | 4/2008 |
| JP | 2011-012143 A | 1/2011 |
| JP | 2011-132275 A | 7/2011 |
| JP | 2011-148973 A | 8/2011 |
| JP | 2012-193308 A | 10/2012 |
| WO | 2012/124791 A1 | 9/2012 |
| WO | 2012/124792 A1 | 9/2012 |

* cited by examiner

*Primary Examiner* — Helene Klemanski
(74) *Attorney, Agent, or Firm* — Canon U.S.A. Inc., IP Division

(57) ABSTRACT

There are provided a new compound which has the following general formula (1) and which is useful as a coloring material, an ink containing the compound, an ink cartridge containing the ink and an ink jet recording method including ejecting the ink from a recording head of an ink jet system to record an image on a recording medium.

general formula (1)

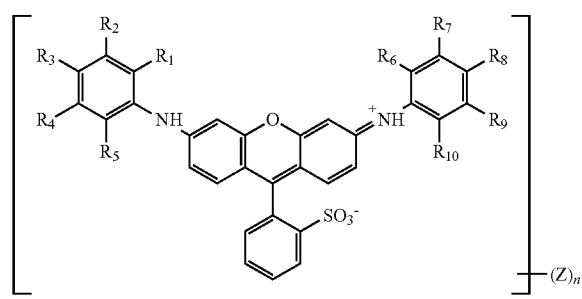

12 Claims, 6 Drawing Sheets

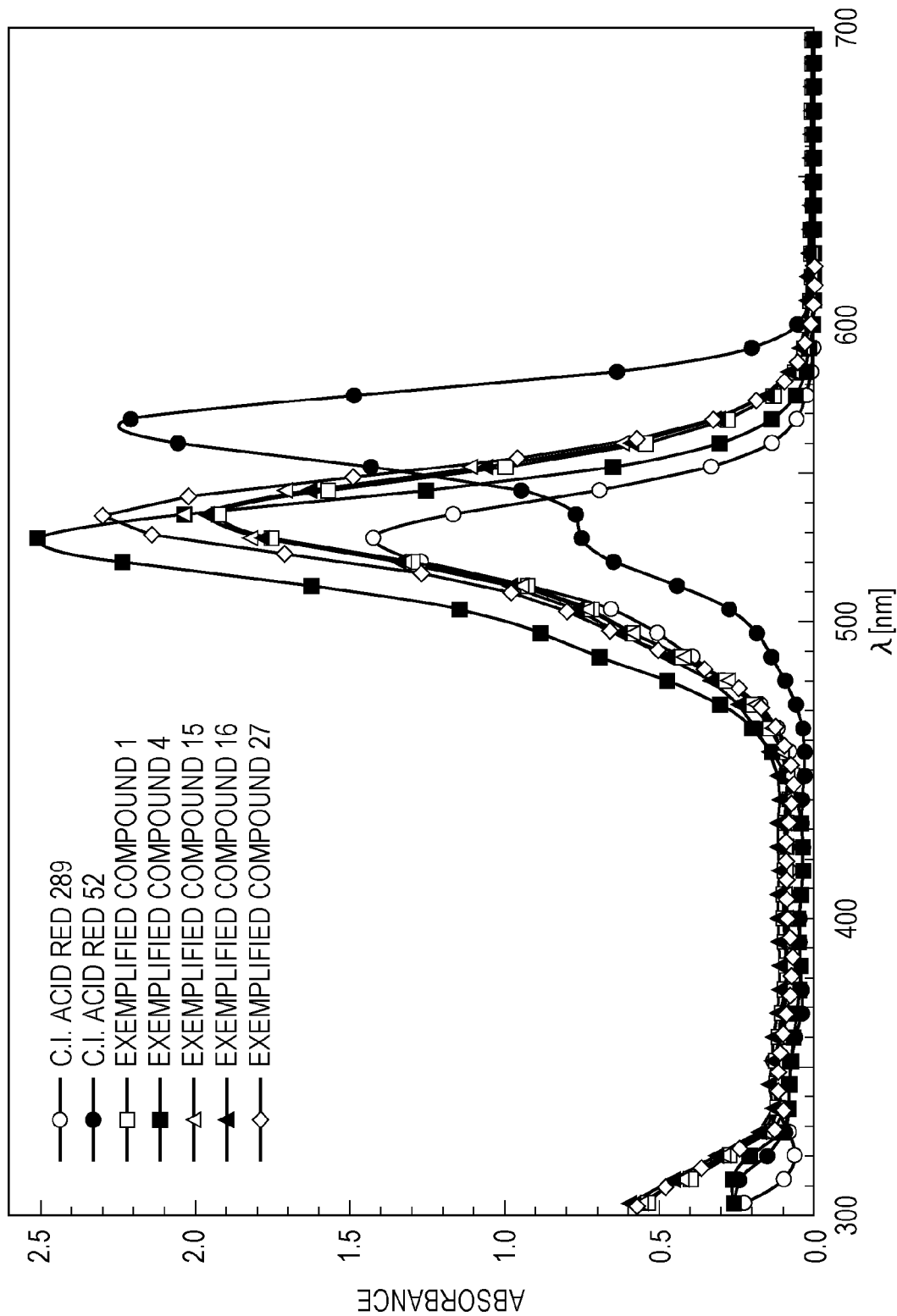

COMPOUND, INK, INK CARTRIDGE AND INK JET RECORDING METHOD

BACKGROUND OF THE INVENTION

1. Field of the Invention

The present invention relates to a new compound useful as a coloring material, an ink containing the compound and so forth.

2. Description of the Related Art

Compounds with xanthene skeletons have been known as coloring materials having magenta hues and good color developability. Each of the compounds with xanthene skeletons has two high absorption bands (x-band and y-band) in the visible region. The complementary colors of the x-band on the side of longer wavelengths and the y-band on the side of shorter wavelengths are mixed together to produce a hue to be visually recognized, thus providing good color developability. Among compounds with xanthene skeletons, C.I. Acid Red 289 is widely known as a coloring material having a magenta hue and very satisfactory color developability and transparency.

However, compounds with xanthene skeletons, typified by C.I. Acid Red 289, in the related art have a problem of low light fastness. To improve the light fastness of compounds with xanthene skeletons, attempts have been made to modify the structure (see Japanese Patent Laid-Open Nos. H09-241553, 2008-094897 and 2011-148973).

Furthermore, compounds with xanthene skeletons are discolored and spread by water in an environment, in other words, disadvantageously have low moisture resistance. In particular, in the case where a compound with a xanthene skeleton is used as a coloring material for an ink jet ink, the compound has been strongly required to have improved moisture resistance in order to form a high-resolution image, which has been required in recent years. To improve the moisture resistance of a compound having a magenta hue, Japanese Patent Laid-Open No. 2011-012143 discloses that the structure of a compound having an anthrapyridone skeleton and the type of counter ion are specified and that an ink is used in combination with specific crown ethers. However, the modification of the structure of a compound having a xanthene skeleton has not been reported from the viewpoint of improving the moisture resistance.

As described above, levels required for the color developability, the light fastness and the moisture resistance of coloring materials have been increased year by year. However, no magenta coloring material that satisfies the foregoing requirement is present. For example, in the compound described in Japanese Patent Laid-Open No. H09-241553 is bluish as compared with C.I. Acid Red 289 and thus has an unsatisfactory hue as a coloring material for magenta. The compound described in Japanese Patent Laid-Open No. 2008-094897 is distinctly bluish as compared with C.I. Acid Red 289 and thus is inadequate to be used as a coloring material for magenta. The compound described in Japanese Patent Laid-Open No. 2011-148973 has satisfactory light fastness but low moisture resistance. Although the ink described in Japanese Patent Laid-Open No. 2011-012143 contains the compound having an anthrapyridone skeleton, the ink is insufficient for the color developability and transparency as magenta.

SUMMARY OF THE INVENTION

An embodiment of the present invention provides a compound useful as a coloring material, the compound having high magenta color developability and excellent light fastness and moisture resistance. Furthermore, an embodiment of the present invention provides an ink containing the compound, an ink cartridge including the ink and an ink jet recording method.

One disclosed aspect of the present invention provides a compound represented by the following general formula (1):

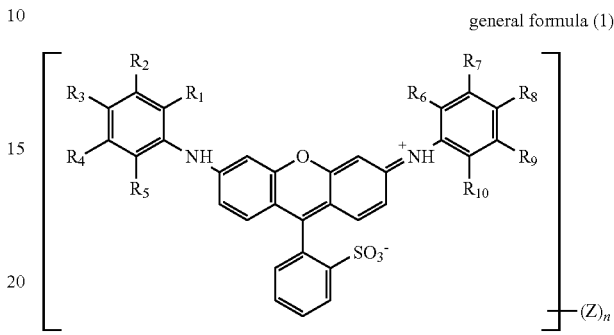

general formula (1)

wherein $R_1$, $R_5$, $R_6$ and $R_{10}$ each independently represent an alkyl group; $R_3$ and $R_8$ each independently represent a hydrogen atom, an alkyl group, an alkoxy group or an aryloxy group; $R_2$, $R_4$, $R_7$ and $R_9$ each independently represent a hydrogen atom, an alkyl group, an alkoxy group, an aryloxy group or a group represented by the general formula (2) described below, at least one of $R_2$, $R_4$, $R_7$ and $R_9$ represents an alkyl group, an alkoxy group or an aryloxy group, and at least one of $R_2$, $R_4$, $R_7$ and $R_9$ represents a group represented by general formula (2) described below; Z independently represents a sulfonic group or a sulfamoyl group; n represents an integer of 0 to 3 when at least one of $R_2$, $R_3$, $R_4$, $R_7$, $R_8$ and $R_9$ contains an ionic group, and n represents an integer of 1 to 3 when none of $R_2$, $R_3$, $R_4$, $R_7$, $R_8$ and $R_9$ contains an ionic group; and when Z is present, Z is substituted for at least one hydrogen atom of an aromatic ring in the general formula (1),

general formula (2)

wherein $R_{11}$ represents an alkyl group, a cycloalkyl group, an aryl group, an aralkyl group, an alkenyl group or a heterocyclic group; and * represents the bonding site of an aromatic ring in the general formula (1).

An embodiment of the present invention provides a compound useful as a coloring material, the compound having high magenta color developability comparable to C.I. Acid Red 289 and overcoming the drawbacks of C.I. Acid Red 289, i.e., having improved light fastness and moisture resistance. Other embodiments of the present invention provide an ink containing the coloring material, an ink cartridge including the ink and an ink jet recording method.

Further features of the present invention will become apparent from the following description of exemplary embodiments with reference to the attached drawings.

BRIEF DESCRIPTION OF THE DRAWINGS

FIG. 6 is a chart illustrating the results of UV/Vis spectral analysis of various compounds (in water, 25° C.).

DESCRIPTION OF THE EMBODIMENTS

Figure 1:
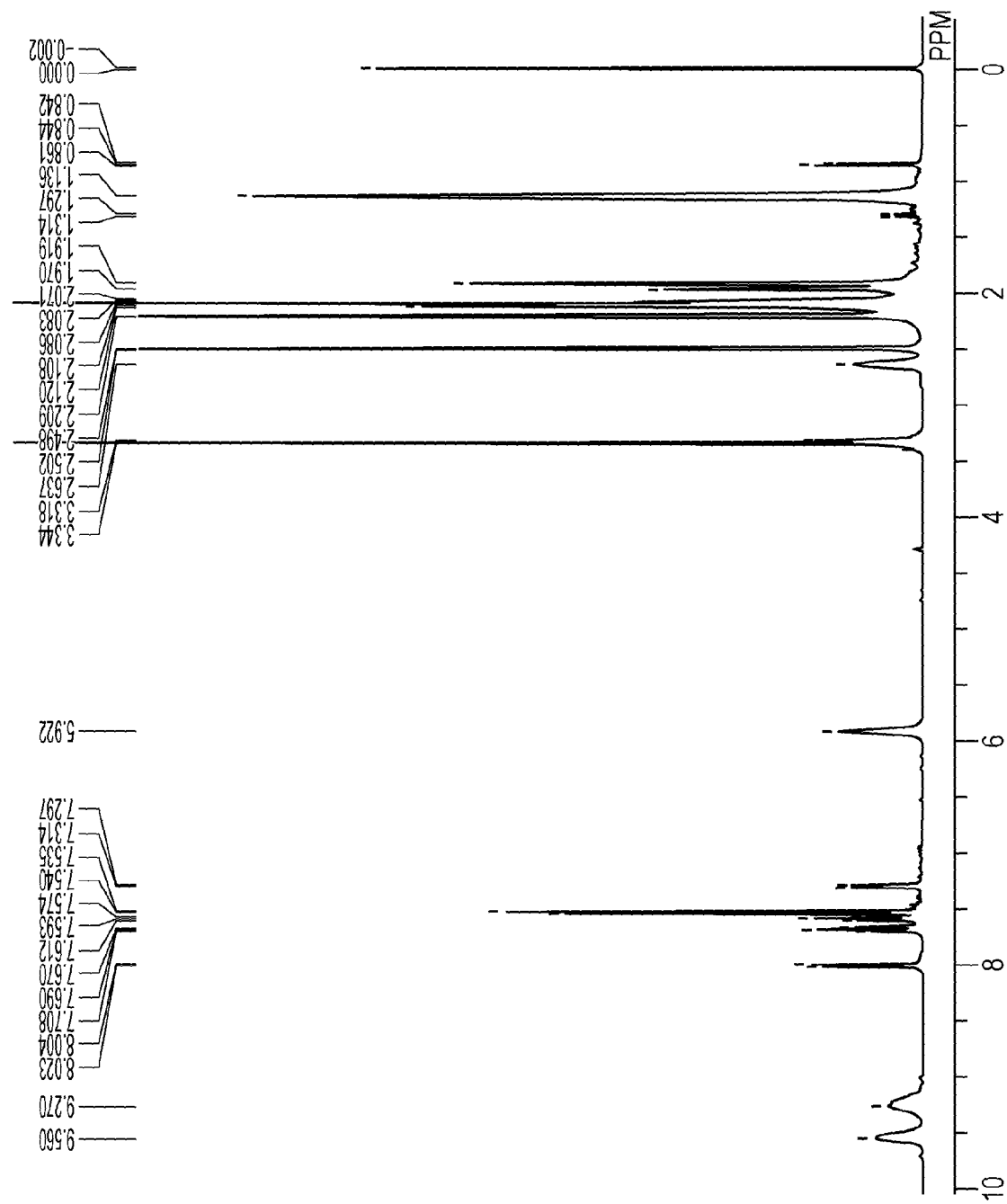
FIG. 1 is a chart illustrating the results of $^1$H NMR analysis of exemplified compound 1.

Embodiments of the present invention will be described in more detail below. In embodiments of the present invention, in the case where a compound is a salt, the salt can be dissociated in an aqueous liquid, such as water or ink, and present in the form of ions. For convenience, however, the ions are referred to as a "salt".

Compound Represented by General Formula (1)

The inventors have conducted studies and have found a compound represented by the general formula (1) as a compound having high magenta color developability comparable to C.I. Acid Red 289 and having excellent light fastness and humidity resistance. In the compound represented by general formula (1), benzene rings bonded to a xanthene skeleton via amino groups are substituted with alkyl groups at the ortho-positions ($R_1$, $R_5$, $R_6$ and $R_{10}$) and are substituted with two specific substituents at any of the meta-positions ($R_2$, $R_4$, $R_7$ and $R_9$) with reference to the bonding position of the amino groups.

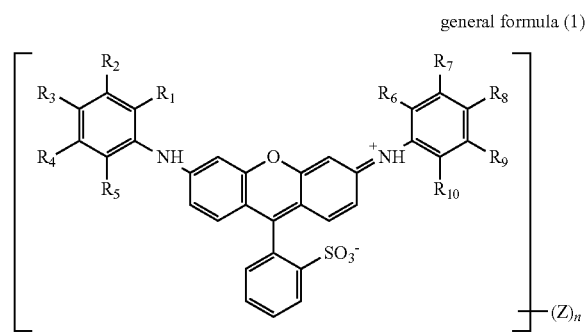

general formula (1)

wherein $R_1$, $R_5$, $R_6$ and $R_{10}$ each independently represent an alkyl group; $R_3$ and $R_8$ each independently represent a hydrogen atom, an alkyl group, an alkoxy group or an aryloxy group; $R_2$, $R_4$, $R_7$ and $R_9$ each independently represent a hydrogen atom, an alkyl group, an alkoxy group, an aryloxy group or a group represented by the general formula (2) described below, at least one of $R_2$, $R_4$, $R_7$ and $R_9$ represents an alkyl group, an alkoxy group or an aryloxy group, and at least one of $R_2$, $R_4$, $R_7$ and $R_9$ represents a group represented by general formula (2) described below; Z independently represents a sulfonic group or a sulfamoyl group; n represents an integer of 0 to 3 when at least one of $R_2$, $R_3$, $R_4$, $R_7$, $R_8$ and $R_9$ contains an ionic group, and n represents an integer of 1 to 3 when none of $R_2$, $R_3$, $R_4$, $R_7$, $R_8$ and $R_9$ contains an ionic group; and when Z is present, Z is substituted for at least one hydrogen atom of an aromatic ring in the general formula (1),

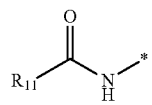

general formula (2)

wherein $R_{11}$ represents an alkyl group, a cycloalkyl group, an aryl group, an aralkyl group, an alkenyl group or a heterocyclic group; and * represents the bonding site of an aromatic ring in the general formula (1).

In the general formula (1), $R_1$, $R_5$, $R_6$ and $R_{10}$ each represent an alkyl group. $R_1$, $R_5$, $R_6$ and $R_{10}$ may have a substituent as long as the spectral reflectance properties, light fastness and moisture resistance of the compound represented by the general formula (1) are not impaired. Examples of the substituent include a hydroxy group; alkoxy groups having 1 to 3 carbon atoms, such as a methoxy group, an ethoxy group and a propoxy group; a cyano group; and halogen atoms, such as a fluorine atom, a chlorine atom and bromine atom.

Examples of the alkyl group of $R_1$, $R_5$, $R_6$ and $R_{10}$ include a straight or a branched alkyl groups having 1 to 6, preferably 1 to 3, carbon atoms. Specific examples of the alkyl group include unsubstituted alkyl groups, such as a methyl group, an ethyl group, a n-propyl group, an isopropyl group, an n-butyl group, an isobutyl group, a sec-butyl group, a tert-butyl group, a 1-methylbutyl group, a n-pentyl group and a n-hexyl group; and substituted alkyl groups, such as a hydroxyethyl group, a methoxyethyl group, a cyanoethyl group and a trifluoromethyl group.

$R_1$, $R_5$, $R_6$ and $R_{10}$ may represent an alkyl group having 1 to 3 carbon atoms because better light fastness is provided. Specific examples thereof include a methyl group, an ethyl group, a n-propyl group and an isopropyl group. When $R_1$, $R_5$, $R_6$ and $R_{10}$ have a substituent, $R_1$, $R_5$, $R_6$ and $R_{10}$ may have the same substituent from the viewpoint of achieving good spectral reflectance properties (for example, color developability, a hue and transparency) and ensuring ease of synthesis.

In the general formula (1), $R_3$ and $R_8$ each independently represent a hydrogen atom, an alkyl group, an alkoxy group or an aryloxy group. $R_3$ and $R_8$ may have a substituent as long as the spectral reflectance properties, light fastness and moisture resistance of the compound represented by the general formula (1) are not impaired. Examples of the substituent include alkyl groups having 1 to 3 carbon atoms, such as a methyl group, an ethyl group, a n-propyl group and an isopropyl group; aryl groups having 6 to 12 carbon atoms, such as a phenyl group and a naphthyl group; aralkyl groups having 7 to 14 carbon atoms, such as a benzyl group, a 2-phenethyl group and a naphthylethyl group; a hydroxy group; a carbamoyl group; a sulfamoyl group; alkoxy groups having 1 to 3 carbon atoms, such as a methoxy group, an ethoxy group, a n-propoxy group and an isopropoxy group; a cyano group; halogen atoms, such as a fluorine atom, a chlorine atom and a bromine atom; and ionic groups, such as anionic groups (for example, a carboxy group, a sulfonic group, a phosphate group and a phosphonate group) and cationic groups (for example, a triethylammonium group and trimethylammonium group).

Examples of the alkyl group of $R_3$ and $R_8$ include straight or branched alkyl groups having 1 to 6, preferably 1 to 3, carbon atoms. Specific examples thereof include unsubstituted alkyl groups, such as a methyl group, an ethyl group, a n-propyl group, an isopropyl group, a n-butyl group, an isobutyl group, a sec-butyl group, a tert-butyl group, a 1-methylbutyl group, a n-pentyl group and a n-hexyl group; and substituted alkyl groups, such as a hydroxyethyl group, a methoxyethyl group, a cyanoethyl group, a trifluoromethyl group, a 3-sulfopropyl group and a 4-sulfobutyl group.

Examples of the alkoxy group of $R_3$ and $R_8$ include straight or branched alkoxy groups having 1 to 6, preferably 1 to 3, carbon atoms. Specific examples thereof include unsubstituted alkoxy groups, such as a methoxy group, an ethoxy group, a n-propoxy group and an isopropoxy group; and substituted alkoxy groups, such as a methoxyethoxy group, a hydroxyethoxy group and a 3-carboxypropoxy group.

Examples of the aryloxy group of $R_3$ and $R_8$ include aryloxy groups having 6 to 12, preferably 6 to 10, carbon atoms. Specific examples thereof include unsubstituted aryloxy groups, such as a phenoxy group and a naphthoxy group; and substituted aryloxy groups, such as a p-methoxyphenoxy group, an o-methoxyphenoxy group, a tolyloxy group and a xylyloxy group.

$R_3$ and $R_8$ may represent an alkyl group having 1 to 3 carbon atoms because better moisture resistance is provided. Specific examples thereof include a methyl group, an ethyl group, a n-propyl group and an isopropyl group. When $R_3$ and $R_8$ have a substituent, $R_3$ and $R_8$ may have the same substituent in view of the ease of synthesis.

In the general formula (1), $R_2$, $R_4$, $R_7$ and $R_9$ each independently represent a hydrogen atom, an alkyl group, an alkoxy group, an aryloxy group or a group represented by the general formula (2), at least one of $R_9$, $R_4$, $R_7$ and $R_9$ represents an alkyl group, an alkoxy group or an aryloxy group, and at least one of $R_9$, $R_4$, $R_7$ and $R_9$ represents a group represented by the general formula (2).

The compound represented by the general formula (1) according to an embodiment of the present invention has high magenta color developability comparable to C.I. Acid Red 289, excellent light fastness and humidity resistance. It is important that at least one of $R_2$, $R_4$, $R_7$ and $R_9$ represent an alkyl group, an alkoxy group or an aryloxy group, and at least one of $R_2$, $R_4$, $R_7$ and $R_9$ represent the group represented by the general formula (2).

$R_2$, $R_4$, $R_7$ and $R_9$ may have a substituent as long as the spectral reflectance properties, light fastness and moisture resistance of the compound represented by the general formula (1) are not impaired. Examples of the substituent include alkyl groups having 1 to 3 carbon atoms, such as a methyl group, an ethyl group, a n-propyl group and an isopropyl group; aryl groups having 6 to 12 carbon atoms, such as a phenyl group and a naphthyl group; aralkyl groups having 7 to 14 carbon atoms, such as a benzyl group, a 2-phenethyl group and a naphthylethyl group; a hydroxy group; a carbamoyl group; a sulfamoyl group; alkoxy groups having 1 to 3 carbon atoms, such as a methoxy group, an ethoxy group, a n-propoxy group and an isopropoxy group; a cyano group; halogen atoms, such as a fluorine atom, a chlorine atom and a bromine atom; and ionic groups, such as anionic groups (for example, a carboxy group, a sulfonic group, a phosphate group and a phosphonate group) and cationic groups (for example, a triethylammonium group and trimethylammonium group).

Examples of the alkyl group of $R_2$, $R_4$, $R_7$ and $R_9$ include a straight or a branched alkyl groups having 1 to 6, preferably 1 to 3, carbon atoms. Specific examples thereof include unsubstituted alkyl groups, such as a methyl group, an ethyl group, a n-propyl group, an isopropyl group, a n-butyl group, an isobutyl group, a sec-butyl group, a tert-butyl group, a 1-methylbutyl group, a n-pentyl group, a n-hexyl group; and substituted alkyl groups, such as a hydroxyethyl group, a methoxyethyl group, a cyanoethyl group, a trifluoromethyl group, a 3-sulfopropyl group and a 4-sulfobutyl group.

Examples of the alkoxy group of $R_2$, $R_4$, $R_7$ and $R_9$ include a straight or a branched alkoxy groups having 1 to 6, preferably 1 to 3, carbon atoms. Specific examples thereof include unsubstituted alkoxy groups, such as a methoxy group, an ethoxy group, a n-propoxy group and an isopropoxy group; and substituted alkoxy groups, such as a methoxyethoxy group, a hydroxyethoxy group and 3-carboxypropoxy group.

Examples of the aryloxy group of $R_2$, $R_4$, $R_7$ and $R_9$ include aryloxy groups having 6 to 12, preferably 6 to 10, carbon atoms. Specific examples thereof include unsubstituted aryloxy groups, such as a phenoxy group and a naphthoxy group; and substituted aryloxy groups, such as a p-methoxyphenoxy group, an o-methoxyphenoxy group, a tolyloxy group and xylyloxy group.

The group represented by the general formula (2) of $R_2$, $R_4$, $R_7$ and $R_9$ is an acylamino group to which $R_{11}$ (for example, an alkyl group, a cycloalkyl group, an aryl group, an aralkyl group, an alkenyl group or a heterocyclic group) is bonded. $R_{11}$ may have a substituent as long as the spectral reflectance properties, light fastness and moisture resistance of the compound represented by the general formula (1) are not impaired. Examples of the substituent include alkyl groups having 1 to 3 carbon atoms, such as a methyl group, an ethyl group, a n-propyl group and an isopropyl group; aryl groups having 6 to 12 carbon atoms, such as a phenyl group and a naphthyl group; aralkyl groups having 7 to 14 carbon atoms, such as a benzyl group, a 2-phenethyl group and a naphthylethyl group; alkenyl groups having 2 to 4 carbon atoms, such as a vinyl group, a 1-propenyl group, a 2-propenyl group, a 1-methylethenyl group, a 1-butenyl group, a 2-butenyl group and a 3-butenyl group; alkoxy groups having 1 to 3 carbon atoms, such as a methoxy group, an ethoxy group, a n-propoxy group and an isopropoxy group; a cyano group; alkylamino groups having 1 to 3 carbon atoms, such as a methylamino group, an ethylamino group, a n-propylamino group and an isopropylamino group; sulfoalkyl groups having 1 to 3 carbon atoms, such as a sulfomethyl group, a sulfoethyl group, a sulfo-n-propyl group and a sulfoisopropyl group; a carbamoyl group; a sulfamoyl group; a sulfonylamino group; halogen atoms, such as a fluorine atom, a chlorine atom and a bromine atom; and ionic groups, such as anionic groups (for example, a carboxy group, a sulfonic group, a phosphate group and a phosphonate group) and cationic groups (for example, a triethylammonium group and trimethylammonium group).

Examples of the alkyl group of $R_{11}$ include a straight or a branched alkyl groups having 1 to 6, preferably 1 to 3, carbon atoms. Specific examples thereof include unsubstituted alkyl groups, such as a methyl group, an ethyl group, a n-propyl group, an isopropyl group, a n-butyl group, an isobutyl group, a sec-butyl group, a tert-butyl group, a 1-methylbutyl group, a n-pentyl group and a n-hexyl group; and substituted alkyl groups, such as a hydroxyethyl group, a methoxyethyl group, a cyanoethyl group, a trifluoromethyl group, a 3-sulfopropyl group and a 4-sulfobutyl group.

Examples of the cycloalkyl group represented by $R_{11}$ include cycloalkyl groups having 3 to 10, preferably 5 to 7, carbon atoms. Specific examples thereof include a cyclopentyl group, a cyclohexyl group and a cycloheptyl group.

Examples of the aryl group represented by $R_{11}$ include aryl groups having 6 to 12, preferably 6 to 10, carbon atoms. Specific examples thereof include unsubstituted aryl groups, such as a phenyl group and a naphthoxy group; and substituted aryl groups, such as a p-tolyl group, a p-methoxyphenyl group, an o-chlorophenyl group, a m-(3-sulfopropylamino) phenyl group and an o-carboxyphenyl group.

Examples of the aralkyl group represented by $R_{11}$ include aralkyl groups having 7 to 14, preferably 7 to 10, carbon atoms. Specific examples thereof include a benzyl group, a 2-phenethyl group and a naphthylethyl group.

Examples of the alkenyl group represented by $R_{11}$ include a straight or a branched alkenyl groups having 2 to 6, preferably 2 to 4 carbon atoms. Specific examples thereof include a vinyl group, a 1-propenyl group, a 2-propenyl group, a 1-methylethenyl group, a 1-butenyl group, a 2-butenyl group and a 3-butenyl group.

The heterocyclic group represented by $R_{11}$ may be a 5- or 6-membered heterocyclic group. Examples of a heteroatom include a nitrogen atom, an oxygen atom and a sulfur atom. The heterocycle may be fused to an aliphatic ring, an aromatic ring and another heterocycle. Examples thereof include an imidazolyl group, a benzoimidazolyl group, a pyrazolyl group, a benzopyrazolyl group, a triazolyl group, a triazolyl group, a benzothiazolyl group, an isothiazolyl group, a benzoisothiazolyl group, an oxazolyl group, a benzoxazolyl group, a thiadiazolyl group, a pyrrolyl group, a benzopyrrolyl group, an indolyl group, an isoxazolyl group, a benzoisoxazolyl group, a thienyl group, a benzothienyl group, a furyl group, a benzofuryl group, a pyridyl group, a quinolyl group, an isoquinolyl group, a pyridazinyl group, a pyrimidinyl group, a pyrazinyl group, a cinnolinyl group, a phthalazinyl group, a quinazolinyl group, a quinoxalinyl group and triazinyl group.

$R_{11}$ may represent an alkyl group, a cycloalkyl group, an aryl group or an aralkyl group because satisfactory color developability is provided. $R_{11}$ may represent an alkyl group or an aryl group because better moisture resistance and light fastness are provided.

At least one of $R_2$, $R_4$, $R_7$ and $R_9$ may represent an alkyl group or an alkoxy group, and the total number of carbon atoms in the alkyl group or the alkoxy group in the compound represented by the general formula (1) may be 2 or more and 8 or less. In this case, the moisture resistance and the solubility in water are improved. In other words, in the case where only one group among $R_2$, $R_4$, $R_7$ and $R_9$ represents an alkyl group or an alkoxy group, the number of carbon atoms therein may be 2 or more and 8 or less. In the case where a plurality of groups among $R_2$, $R_4$, $R_7$ and $R_9$ represent an alkyl group or an alkoxy group, the number of carbon atoms therein may be 2 or more and 8 or less. In particular, a plurality of groups among $R_2$, $R_4$, $R_7$ and $R_9$ represent an alkyl group or an alkoxy group, and the number of carbon atoms therein may be 2 or more and 8 or less. Furthermore, two of $R_2$, $R_4$, $R_7$ and $R_9$ may represent a group represented by the general formula (2) because better moisture resistance is provided.

In the case where the compound represented by the general formula (1) contains two or more groups represented by the general formula (2), the two or more groups represented by the general formula (2) may have the same structure in view of the ease of synthesis of the compound represented by the general formula (1). Furthermore, both of $R_2$ and $R_7$ may represent the group represented by the general formula (2), and both of $R_4$ and $R_9$ may represent an alkyl group. $R_1$ and $R_6$ may represent the same group. $R_2$ and $R_7$ may represent the same group. $R_3$ and $R_8$ may represent the same group. $R_4$ and $R_9$ may represent the same group. $R_5$ and $R_{10}$ may represent the same group. That means each of the combination of $R_1$ and $R_6$, $R_2$ and $R_7$, $R_3$ and $R_8$, and $R_5$ and $R_{10}$ may represent the same group.

In the general formula (1), Z independently represents a sulfonic group or a sulfamoyl group. n represents an integer of 0 to 3 when at least one of $R_2$, $R_3$, $R_4$, $R_7$, $R_8$ and $R_9$ contains an ionic group. n represents an integer of 1 to 3 when none of $R_2$, $R_3$, $R_4$, $R_7$, $R_8$ and $R_9$ contains an ionic group. When Z is present, Z is substituted for at least one hydrogen atom of an aromatic ring in the general formula (1). Examples of the ionic group that may be contained in at least one of $R_2$, $R_3$, $R_4$, $R_7$, $R_8$ and $R_9$ include anionic groups, such as a carboxy group, a sulfonic group, a phosphate group and a phosphonate group; and cationic groups, such as a triethylammonium group and trimethylammonium group.

n indicates the number of Z serving as a substituent in the general formula (1) and represents an integer of 0 to 3. Specifically, when n=0, the compound represented by the general formula (1) does not contain a sulfonic group or a sulfamoyl group as Z. In this case, at least one of $R_2$, $R_3$, $R_4$, $R_7$, $R_8$ and $R_9$ needs to contain an ionic group in order to ensure the solubility of the compound in water. When at least one of $R_2$, $R_3$, $R_4$, $R_7$, $R_8$ and $R_9$ contains an ionic group, the compound can dissolve in water owing to the ionic group. Thus, n may represent 0. According to an embodiment of the present invention, n may represent 1 or more because of better solubility in water. n may represent 3 or less in order to provide high moisture resistance. The compound represented by the general formula (1) may be a mixture of a plurality of compounds having different values of n.

The sulfonic group represented by Z may be of the form of acid or salt. In the case of a sulfonic group in the form of a salt, while at least part of the sulfonic group in the form of a salt may be ionically dissociated in an aqueous ink to form a counter ion, the group is referred to as the "sulfonic group in the form of a salt" in this specification, for convenience.

In the case of a sulfonic group in the form of a salt, examples of the counter ion to form a salt include ions of alkali metals, such as lithium, sodium and potassium; an unsubstituted ammonium ion; and ions of organic ammonium, such as methylammonium, dimethylammonium, trimethylammonium, tetramethylammonium, ethylammonium, diethylammonium, triethylammonium, tetraethylammonium, n-propylammonium, isopropylammonium, diisopropylammonium, n-butylammonium, tetra-n-butylammonium, isobutylammonium, monoethanolammonium, diethanolammonium and triethanolammonium. In addition to the sulfonic group represented by Z, the ionic group that may be represented by at least one of $R_2$, $R_3$, $R_4$, $R_7$, $R_8$ and $R_9$ may also be of the type of acid or salt. For example, in the case of an anionic group in the form of a salt, examples of a counter ion include the same counter ions as described above.

The sulfamoyl group represented by Z may have a substituent as long as the spectral reflectance properties, light fastness and moisture resistance of the compound represented by the general formula (1) are not impaired. Examples of the substituent include alkyl groups having 1 to 3 carbon atoms, such as a methyl group, an ethyl group, a n-propyl group and an isopropyl group. Examples of the sulfamoyl group include an unsubstituted sulfamoyl group (aminosulfonyl group); and sulfamoyl groups each substituted with an alkyl group having 1 to 4 carbon atoms, such as a methylaminosulfonyl group, a dimethylaminosulfonyl group and a butylaminosulfonyl group.

According to an embodiment of the present invention, the compound represented by the general formula (1) may have an anionic group in the form of a salt because the solubility of the compound in water is increased. Specifically, in the general formula (1), n represents an integer of 1 to 3, and Z represents a sulfonic group in the form of a salt. In this case, the counter ion of the sulfonic group may be preferably at least one selected from the group consisting of a lithium ion, a sodium ion and an ammonium ion.

The substitution position of Z in the main skeleton of the compound represented by the general formula (1) (i.e., a structure within parentheses in the general formula (1)) depends on substitution positions of other substituents in the general formula (1) and reaction conditions for sulfonation or chlorosulfonation. In the case where all of $R_2$, $R_3$, $R_4$, $R_7$, $R_8$ and $R_9$ represents a substituent other than a hydrogen atom and where a substituent on $R_{11}$ does not have an aromatic hydrogen atom, Z is substituted only for a hydrogen atom of a xanthene skeleton. In the case where at least one of $R_2$, $R_3$, $R_4$, $R_7$, $R_8$ and $R_9$ represents a hydrogen atom, Z may be substituted for the hydrogen atom. In the case where $R_{11}$ has an aromatic ring and an aromatic hydrogen atom, an aromatic ring may be substituted with Z. In an embodiment of the present invention, Z may be substituted for a hydrogen atom on the xanthene skeleton in view of the ease of synthesis.

The compound represented by the general formula (1) has tautomers. Examples of the tautomers include compounds represented by the general formulae (1a) and (1b) in addition to the compound represented by the general formula (1). In an embodiment of the present invention, the compound represented by the general formula (1) includes these compounds (tautomers) and their salts. $R_1$ to $R_{10}$ in the general formulae (1a) and (1b) are defined the same as $R_1$ to $R_{10}$ in the general formula (1).

The compound represented by the general formula (1) may be synthesized on the basis of a known method. An example of a synthetic scheme is described below. $R_1$ to $R_{10}$, Z and n in compounds (B), (C), (D) and (E) illustrated in the synthetic scheme are defined the same as $R_1$ to $R_{10}$, Z and n in the general formula (1). The compound represented by the general formula (1) may be synthesized as a mixture of a plurality of isomers, which differ in the types, numbers and positions of substituents. According to an embodiment of the present invention, for convenience, the term "compound" includes the mixture.

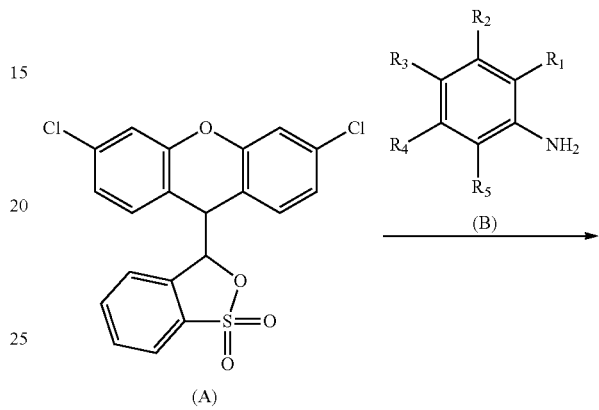

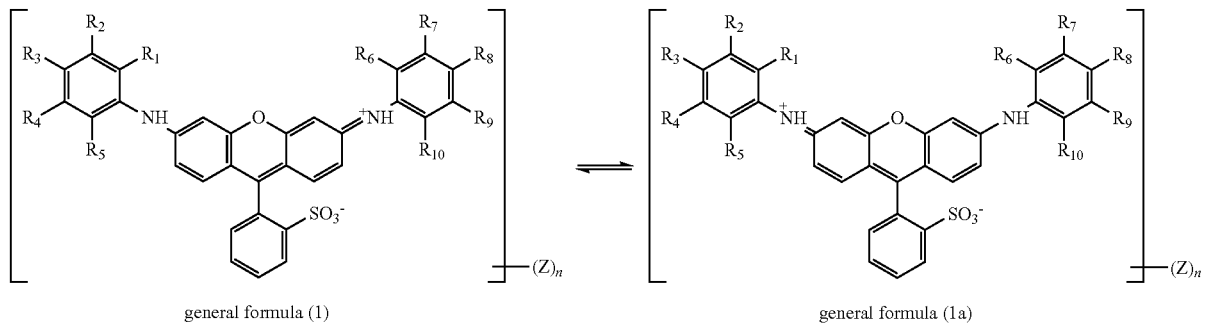

general formula (1)    general formula (1a)

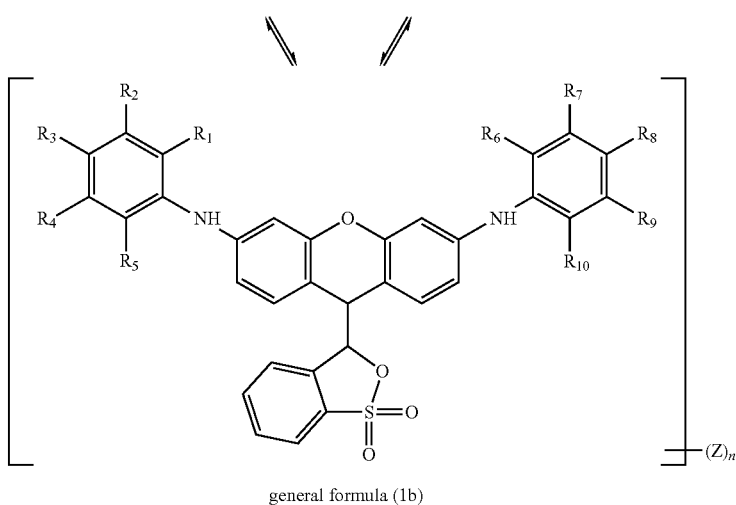

general formula (1b)

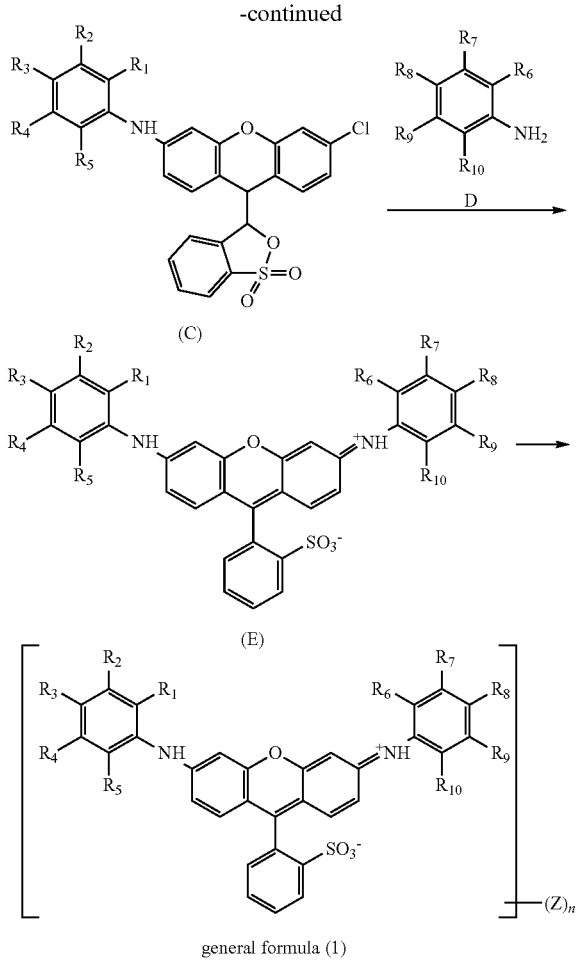

general formula (1)

In the exemplified synthetic scheme, the compound represented by the general formula (1) is synthesized through a first condensation step illustrated in the first row, a second condensation step illustrated in the second row, and a sulfamoylation step illustrated in the third row. However, in the case where at least one of $R_2$, $R_3$, $R_4$, $R_7$, $R_8$ and $R_9$ contains an ionic group as a substituent, the sulfonation or sulfamoylation step may not be performed.

First, in the first condensation step, compound (A) and compound (B) are condensed by heating in the presence of an organic solvent and a condensing agent, thereby forming compound (C). Then in the second condensation step, compound (D) and compound (C) formed in the first condensation step are condensed by heating to form compound (E). Finally, compound (E) formed in the second condensation step is sulfonated with a sulfonating agent, for example, concentrated sulfuric acid or fuming sulfuric acid, thereby forming the compound represented by the general formula (1) in which Z represents a sulfonic group. Alternatively, compound (E) formed in the second condensation step is subjected to chlorosulfonation with, for example, chlorosulfonic acid and then sulfamoylation by reaction with an amine compound, for example, concentrated aqueous ammonia, an alkylamine or an arylamine, thereby forming the compound represented by the general formula (1) in which Z represents a sulfonic group.

The organic solvent used in the synthetic scheme illustrated above will be described below. In the first condensation step, for example, methanol, ethanol, n-propanol, isopropyl alcohol and n-butanol may be used separately or in combination as a mixture. In the second condensation step, for example, ethylene glycol, N-methylpyrrolidone, N,N-dimethylacetamide, N,N-dimethylformamide, dimethyl sulfoxide, sulfolane, chlorobenzene, dichlorobenzene, trichlorobenzene and nitrobenzene may be used separately or in combination as a mixture.

The reaction temperature in the first condensation step is preferably in the range of 60° C. to 100° C. and more preferably 70° C. or higher and 90° C. or lower. The reaction temperature in the second condensation step is preferably in the range of 120° C. to 220° C. and more preferably 180° C. or lower.

In the case where a compound represented by the general formula (1) in which $R_1$ to $R_5$ are the same group and $R_6$ to $R_{10}$ are the same group is synthesized, compounds (B) and (D) used in the foregoing synthetic scheme may be identical. In this case, thus, compound (E) may be formed through a single condensation step from compound (A). The reaction temperature is preferably in the range of 120° C. to 220° C. and more preferably 180° C. or lower. Examples of the condensing agent that may be used include magnesium oxide, zinc chloride and aluminum chloride.

The compound, which is an end product, synthesized by the synthetic scheme is treated according to a common post-treatment method for reaction in organic synthesis and then purified. As a result, the compound may be used for desired applications, for example, a coloring material (dye) for ink. The compound represented by the general formula (1) may be identified by the use of, for example, $^1$H NMR analysis, LC/MS analysis and UV/Vis spectral analysis.

The compound represented by the general formula (1) according to an embodiment of the present invention has high magenta color developability and excellent light fastness and moisture resistance. The compound represented by the general formula (1) may be suitably used as a coloring material for use in various inks for printing, coating, writing implements, ink jet recording and so forth. In addition to various inks, the compound represented by the general formula (1) may be suitably used as a coloring material for optical recording, color filters and so forth.

Ink

An ink according to an embodiment of the present invention contains the foregoing compound represented by the general formula (1) as a coloring material (dye) and is suitable as an ink jet ink. The content (% by mass) of the compound represented by the general formula (1) in the ink is preferably 0.10% by mass or more and 10.00% by mass or less and more preferably 0.20% by mass or more and 5.00% by mass or less with respect to the total mass of the ink.

Other components contained in the ink according to an embodiment of the present invention will be described below.

Another Coloring Material

The inventors have found that an ink containing a compound which serves as a coloring material and which has a different structure from that of the compound represented by the general formula (1) in addition to the compound represented by the general formula (1) has further improved light fastness without reducing the excellent moisture resistance of the compound represented by the general formula (1).

Examples of the compound (another coloring material) which has a different structure from that of the compound represented by the general formula (1) and which may be used in addition to the compound represented by the general formula (1) include pigments and dyes. A dye may be used. A compound having any hue, for example, cyan, magenta, yellow, red, blue, green or black, may be used as another coloring material. In particular, a dye having a hue ranging from magenta to red may be used. A dye of a compound having an azo skeleton or anthrapyridone skeleton may be used. Specifically, a compound having a maximum absorption wavelength ($\lambda_{max}$) in water of 380 to 590 nm, preferably 480 to 570 nm, and more preferably 500 to 560 nm may be used from the viewpoint of achieving the effect of further improving color developability.

Specific examples of the compound having an azo skeleton or anthrapyridone skeleton include compounds having the following structures in the form of free acids. Embodiments of the present invention are not limited to the following compounds.

An example of the compound having an azo skeleton is a compound described in Japanese Patent Laid-Open No. 2006-143989. Specifically, azo compound 1 ($\lambda_{max}$=555 nm) illustrated blow may be used. Furthermore, azo compound 2 ($\lambda_{max}$=523 nm), i.e., C.I. Acid Red 249 may also be used.

azo compound 1

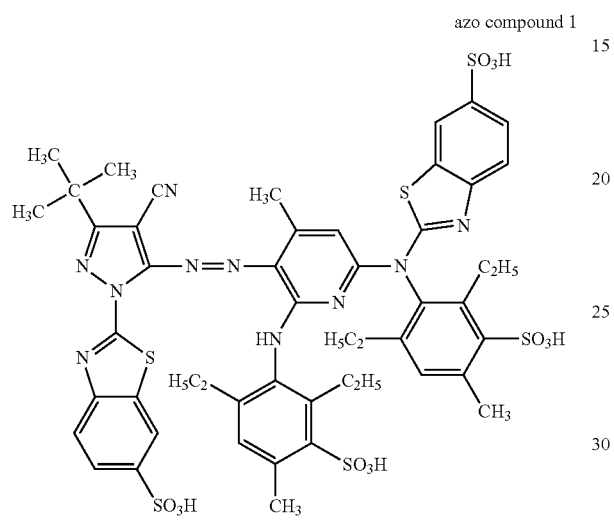

azo compound 2

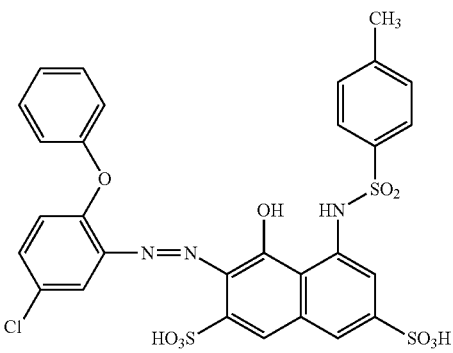

Examples of the compound having an anthrapyridone skeleton include compounds described in Japanese Patent Laid-Open Nos. H10-306221 and 2010-006969. Specifically, anthrapyridone compound 1 ($\lambda_{max}$=530 nm) and anthrapyridone compound 2 ($\lambda_{max}$=510 nm) may be used.

anthrapyridone compound 1

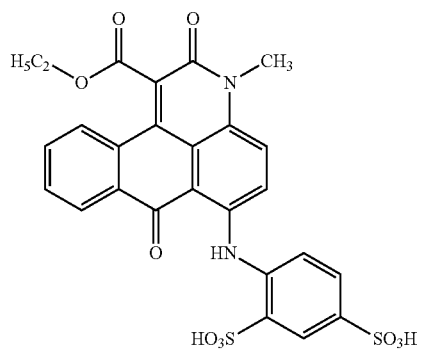

anthrapyridone compound 2

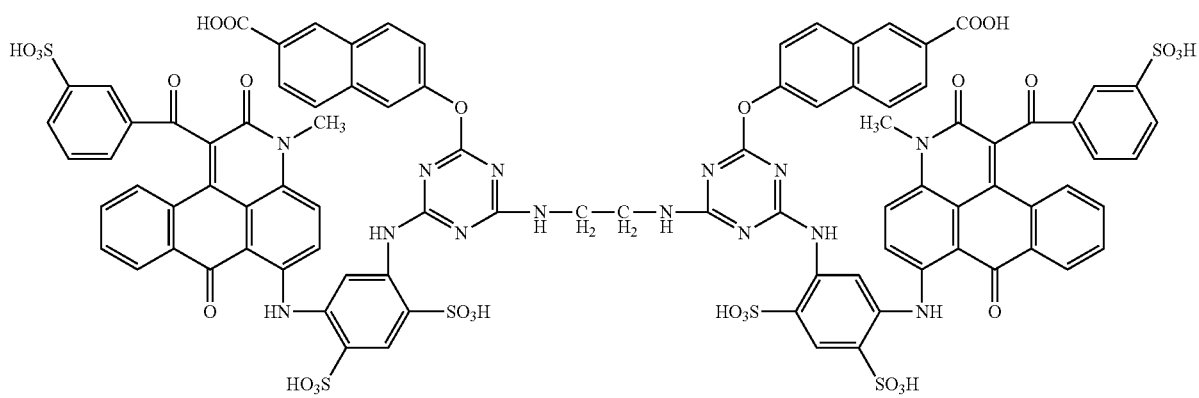

In the case where the compound having a different structure from that of the compound represented by the general formula (1) is used as a coloring material in an ink, the content (% by mass) of the compound in the ink is preferably 0.10% by mass or more and 10.00% by mass or less and more preferably 0.30% by mass or more and 5.00% by mass or less with respect to the total mass of the ink. In the case where the compound having a different structure from that of the compound represented by the general formula (1) is used as a coloring material in an ink in addition to the compound represented by the general formula (1), the contents of the compounds may be set as described below. To achieve a higher level of magenta color developability, the content (% by mass) of the compound represented by the general formula (1) in the ink may be 0.35% by mass or more with respect to the total mass of the ink. In this case, the upper limit of the content (% by mass) of the compound represented by the general formula (1) in the ink may be 10.00% by mass or less, preferably 5.00% by mass or less, as with the foregoing case. The total content (% by mass) of the compounds (coloring materials) in the ink may be 0.10% by mass or more and 10.00% by mass or less with respect to the total mass of the ink.

The inventors have conducted studies and have found that in the case where the compound represented by the general formula (1) and the compound having a different structure from that of the compound represented by the general formula (1) are contained in an ink in a specific mass ratio, it is possible to further improve the light fastness with the color developability and the moisture resistance maintained at high levels. Specifically, with respect to the total mass of the ink, the mass ratio of the content (% by mass) of the compound represented by the general formula (1) to the content (% by mass) of the compound having a different structure from that of the compound represented by the general formula (1) is preferably 0.1 times or more and 9.0 times or less and more preferably 0.1 times or more and 1.0 time or less.

Aqueous Medium

Water or an aqueous medium that is a mixed medium of water and a water-soluble organic solvent may be used for the ink according to an embodiment of the present invention. Deionized water (ion-exchanged water) may be used as water. The content (% by mass) of water in the ink may be 10.0% by mass or more and 90.0% by mass or less with respect to the total mass of the ink.

The water-soluble organic solvent is not particularly limited as long as it is soluble in water. Examples thereof include monohydric and polyhydric alcohols, alkylene glycols, glycol ethers, nitrogen-containing polar compounds and sulfur-containing polar compounds. The content (% by mass) of the water-soluble organic solvent in the ink is preferably 5.0% by mass or more and 90.0% by mass or less and more preferably 10.0% by mass or more and 50.0% by mass or less with respect to the total mass of the ink. In the case where the ink is used as an ink jet ink, it is possible to provide satisfactory ejection stability of the ink ejected from a recording head when the content of the water-soluble organic solvent is within the foregoing range.

Additional Additives

The ink according to an embodiment of the present invention may optionally contain a water-soluble organic compound that is solid at normal temperature, such as a polyhydric alcohol, such as trimethylol propane or trimethylol ethane, urea, or a urea derivative, such as ethylene urea, in addition to the foregoing component. The ink according to an embodiment of the present invention may optionally contain various additives, such as a surfactant, a pH adjuster, a preservative, a fungicide, an antioxidant, a reduction inhibitor, an evaporation promoter, a chelating agent and a water-soluble resin.

Ink Cartridge

An ink cartridge according to an embodiment of the present invention includes an ink and an ink storage portion. The ink stored in the ink storage portion is the foregoing ink according to an embodiment of the present invention.

Ink Jet Recording Method

An ink jet recording method according to an embodiment of the present invention is a method in which the foregoing ink according to an embodiment of the present invention is ejected from a recording head of an ink jet system to record an image on a recording medium. Examples of a method for ejecting an ink include a method in which mechanical energy is applied to an ink; and a method in which thermal energy is applied to an ink. In an embodiment of the present invention, a method in which thermal energy is applied to an ink may be employed. The ink jet recording method may include known steps, except that the ink according to an embodiment of the present invention is used.

EXAMPLES

While the present invention will be described in more detail below by examples and comparative examples, the present invention is not limited to these examples so long as the invention does not depart from the scope thereof. Regarding the amount of a component, "part(s)" and "%" are expressed on a mass basis unless otherwise specified.

Identification of Compound Represented by General Formula (1)

A compound represented by the general formula (1) synthesized as described below was identified by the following analytical method:

(1) $^1$H NMR analysis: a $^1$H nuclear magnetic resonance spectrometer (ECA-400, manufactured by JEOL Ltd);

(2) LC/MS analysis: LC/TOF MS (LC/MSD TOF, manufactured by Agilent Technologies), an electrospray ionization (ESI) method was employed as an ionization method; and (3) UV/Vis spectral analysis: an UV/Vis spectrophotometer (UV-3600 spectrophotometer, manufactured by Shimadzu Corporation).

Synthesis of Compound Represented by the General Formula (1)

Exemplified Compound 1

First, 3-isobutyrylamino-2,4,5,6-tetramethylaniline (8.9 g) and compound (A) (7.4 g) in the foregoing synthetic scheme were reacted in sulfolane (20 mL) in the presence of zinc chloride (4.1 g) by heating at 150° C. for 3 hours. The resulting solution was cooled and then added to 50 mL of 2 mol/L hydrochloric acid to precipitate crystals. The precipitated crystals was separated by filtration, washed with water, and dried. Then 6 g of the resulting dry product was added to 30 g of ice-cold fuming sulfuric acid and then stirred at 20° C. to 25° C. for 4 hours. The reaction liquid was poured on 100 g of ice. The precipitated sulfonated product was separated by filtration and washed with cold water to give a precipitate. The resulting precipitate was suspended in 50 mL of water. The pH of the resulting suspension was adjusted to 7.0 with a 2 mol/L aqueous solution of sodium hydroxide to form a solution. Crystallization was performed with acetone to give exemplified compound 1 represented by a structural formula described below.

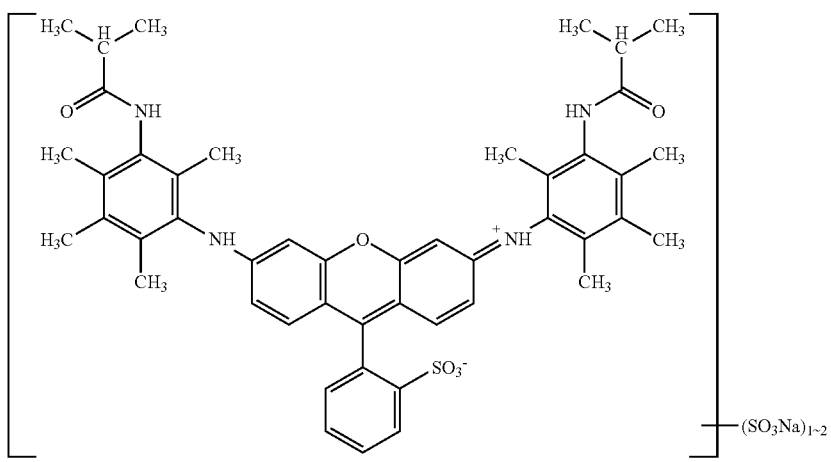

exemplified compound 1

The analysis of exemplified compound 1 by (1) $^1$H NMR analysis, (2) LC/TOF MS analysis and (3) UV/Vis spectral analysis demonstrated that exemplified compound 1 had the foregoing structure. The analytical results are described below.

(1) Results of $^1$H NMR (400 MHz, DMSO-d$_6$, room temperature) (see FIG. 1):

δ [ppm]=9.56 (br, 2H), 9.27 (br, 2H), 8.01 (d, 1H), 7.69 (t, 1H), 7.59 (t, 1H), 7.54 (s, 1H), 7.53 (s, 1H), 7.31 (d, 1H), 5.92 (s, 2H), 2.64 (s, 2H), 2.30-1.80 (m, 24H), 1.14 (s, 12H);

(2) Results of LC/TOF MS analysis (eluent: 0.1% aqueous solution of acetic acid-methanol, ESI):

retention time: 10.1 minutes, purity=58.7% by area, 959.27 (n=2, [M-2Na+H]$^-$), retention time: 12.7 minutes, purity=40.5% by area, m/z=959.27 (n=2, [M-2Na+H]$^-$);

(3) Results of UV/Vis spectral analysis (see FIG. 6):

$\lambda_{max}$=535 nm, ε=77410 M$^{-1}$ cm$^{-1}$ (in water, 25° C.)

Exemplified Compound 4

First, 3-isobutyrylamino-5-ethoxy-2,4,6-trimethylaniline (10.0 g) and compound (A) (7.4 g) in the foregoing synthetic scheme were reacted in sulfolane (20 mL) in the presence of zinc chloride (4.1 g) by heating at 150° C. for 3 hours. The resulting solution was cooled and then added to 50 mL of 2 mol/L hydrochloric acid to precipitate crystals. The precipitated crystals was separated by filtration, washed with water, and dried. Then 6 g of the resulting dry product was added to 30 g of ice-cold fuming sulfuric acid and then stirred at 20° C. to 25° C. for 4 hours. The reaction liquid was poured on 100 g of ice. The precipitated sulfonated product was separated by filtration and washed with cold water to give a precipitate. The resulting precipitate was suspended in 50 mL of water. The pH of the resulting suspension was adjusted to 7.0 with a 2 mol/L aqueous solution of sodium hydroxide to form a solution. Crystallization was performed with acetone to give exemplified compound 4 represented by a structural formula described below.

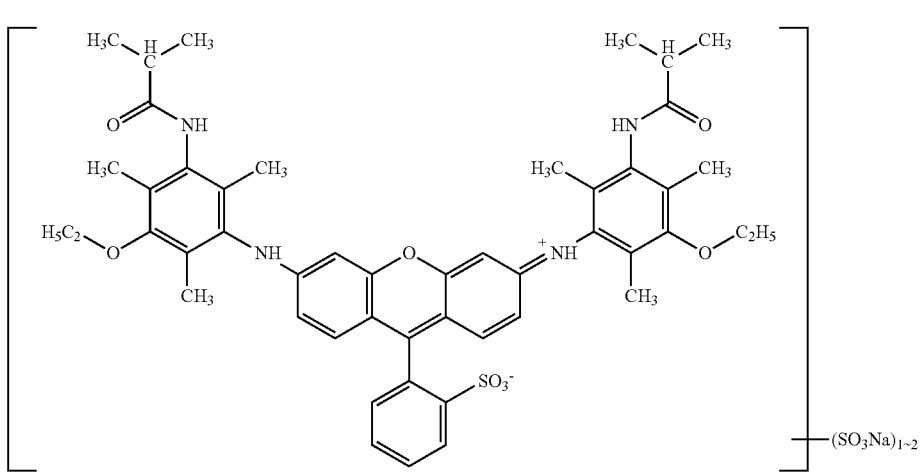

exemplified compound 4

The analysis of exemplified compound 4 by (1) $^1$H NMR analysis, (2) LC/TOF MS analysis and (3) UV/Vis spectral analysis demonstrated that exemplified compound 4 had the foregoing structure. The analytical results are described below.

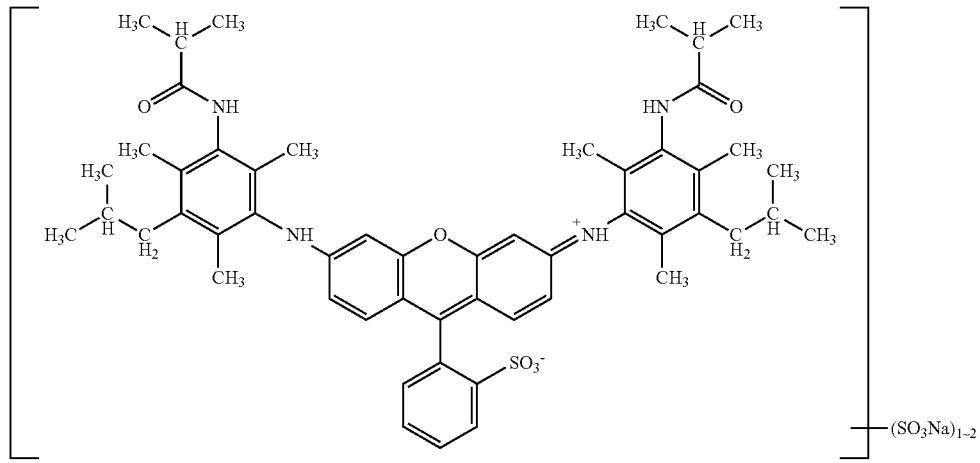

exemplified compound 15

Figure 2:
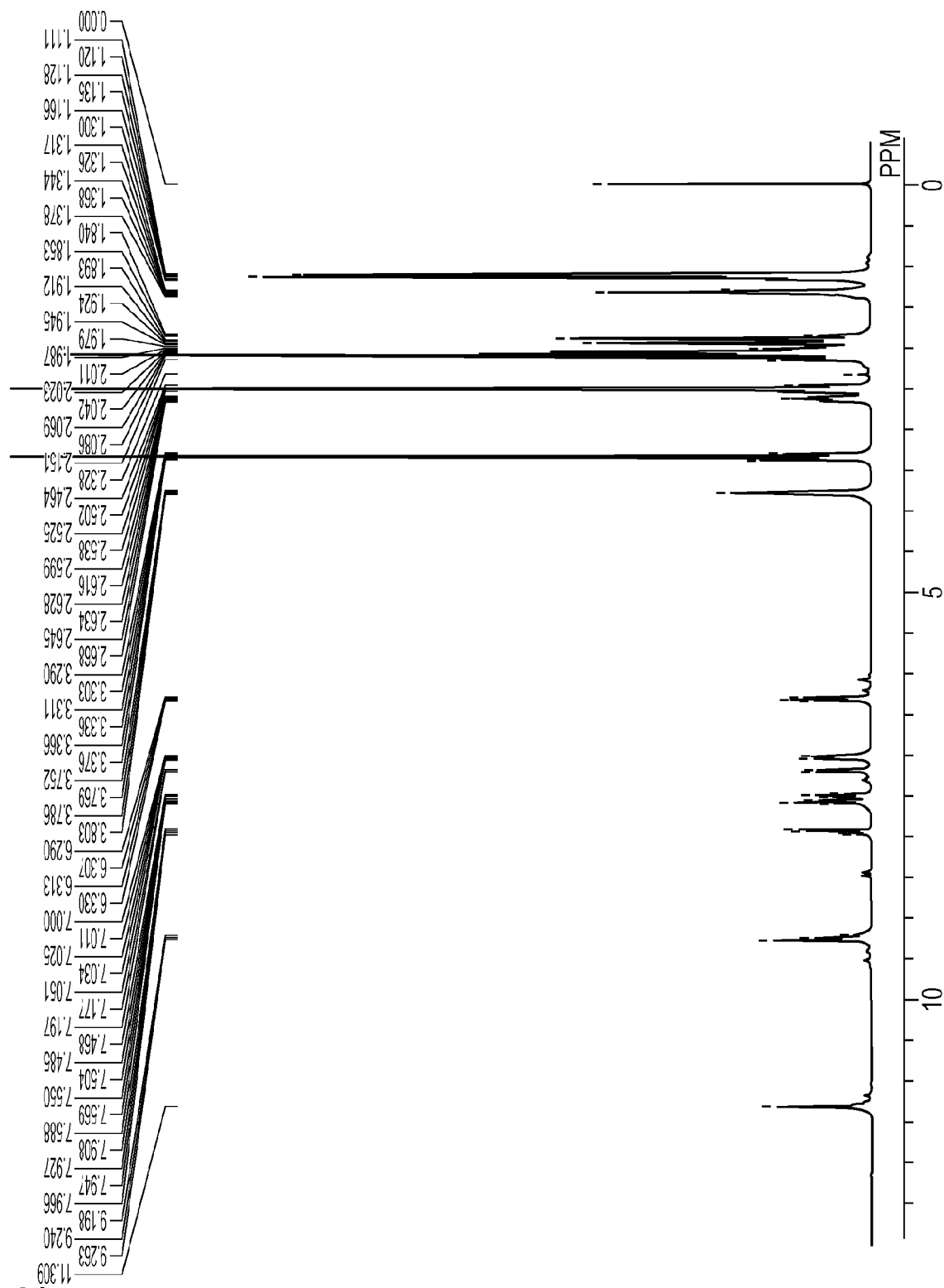
FIG. 2 is a chart illustrating the results of $^1$H NMR analysis of exemplified compound 4.

(1) Results of $^1$H NMR (400 MHz, DMSO-$d_6$, room temperature) (see FIG. 2):

δ [ppm]=11.31 (s, 2H), 9.25 (d, 2H), 7.91 (d, 1H), 7.70-7.40 (m, 2H), 7.18 (d, 1H), 7.10-6.90 (m, 2H), 6.33-6.07 (m, 2H), 3.78 (q, 4H), 2.67-2.62 (m, 2H), 2.15-1.84 (m, 18H), 1.38-1.11 (m, 18H);

(2) Results of LC/TOF MS analysis (eluent: 0.1% aqueous solution of acetic acid-methanol, ESI):

retention time: 7.9 minutes, purity=30.0% by area, m/z=1019.29 (n=2, [M-2Na+H]$^-$), retention time: 9.7 minutes, purity=43.1% by area, m/z=1019.30 (n=2, [M-2Na+H]$^-$), retention time: 11.4 minutes, purity=20.9% by area, m/z=1019.29 (n=2, [M-2Na+H]$^-$), retention time: 14.3 minutes, purity=3.5% by area, m/z=939.33 (n=1, [M−Na+H]$^-$), retention time: 16.0 minutes, purity=5.2% by area, m/z=939.33 (n=1, [M−Na+H]$^-$);

(3) Results of UV/Vis spectral analysis (see FIG. 6):

$\lambda_{max}$=535 nm, $\epsilon$=100552 M$^{-1}$ cm$^{-1}$ (in water, 25° C.)

Exemplified Compound 15

First, 3-isobutyrylamino-5-isobutyl-2,4,6-trimethylaniline (10.5 g) and compound (A) (7.4 g) in the foregoing synthetic scheme were reacted in sulfolane (20 mL) in the presence of zinc chloride (4.1 g) by heating at 150° C. for 3 hours. The resulting solution was cooled and then added to 50 mL of 2 mol/L hydrochloric acid to precipitate crystals. The precipitated crystals was separated by filtration, washed with water, and dried. Then 6 g of the resulting dry product was added to 30 g of ice-cold concentrated sulfuric acid and then stirred at 20° C. to 25° C. for 4 hours. The reaction liquid was poured on 100 g of ice. The precipitated sulfonated product was separated by filtration and washed with cold water to give a precipitate. The resulting precipitate was suspended in 50 mL of water. The pH of the resulting suspension was adjusted to 7.0 with a 2 mol/L aqueous solution of sodium hydroxide to form a solution. Crystallization was performed with acetone to give exemplified compound 15 represented by a structural formula described below.

The analysis of exemplified compound 15 by (1) $^1$H NMR analysis, (2) LC/TOF MS analysis and (3) UV/Vis spectral analysis demonstrated that exemplified compound 15 had the foregoing structure. The analytical results are described below.

Figure 3:
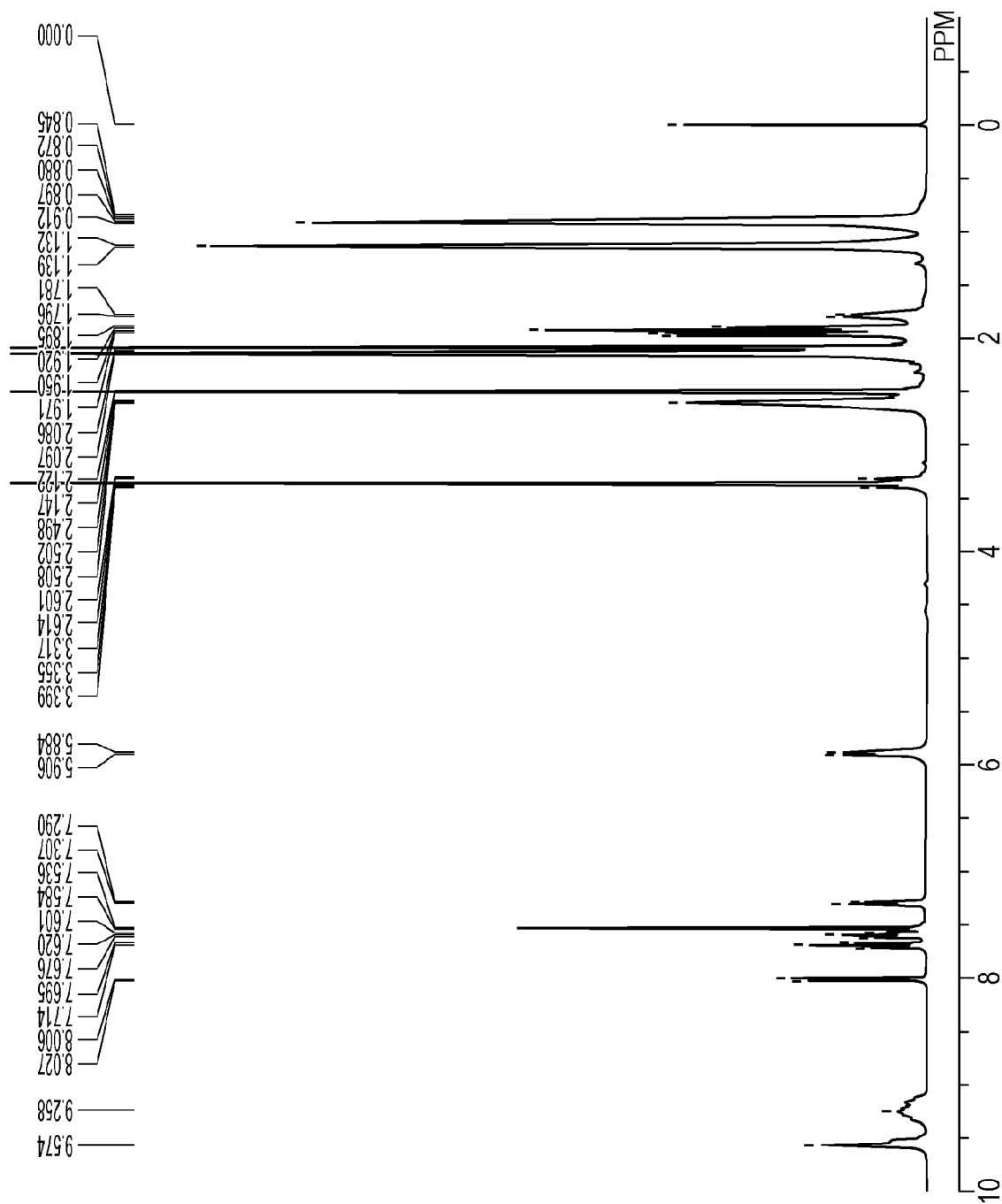
FIG. 3 is a chart illustrating the results of $^1$H NMR analysis of exemplified compound 15.

(1) Results of $^1$H NMR (400 MHz, DMSO-$d_6$, room temperature) (see FIG. 3):

δ [ppm]=9.57 (brs, 2H), 9.23 (br, 2H), 8.02 (d, 1H), 7.70 (t, 1H), 7.60 (t, 1H), 7.54 (s, 2H), 7.30 (d, 1H), 5.90 (d, 2H), 2.61 (d, 4H), 2.15-1.78 (m, 22H), 1.14-0.85 (m, 24H);

(2) Results of LC/TOF MS analysis (eluent: 0.1% aqueous solution of acetic acid-methanol, ESI):

retention time: 15.1 minutes, purity=57.1% by area, m/z=1043.36 (n=2, [M-2Na+H]$^-$), retention time: 16.9 minutes, purity=42.4% by area, m/z=1043.36 (n=2, [M-2Na+H]$^-$);

(3) Results of UV/Vis spectral analysis (see FIG. 6):

$\lambda_{max}$=528 nm, $\epsilon$=81796 M$^{-1}$ cm$^{-1}$ (in water, 25° C.)

Exemplified Compound 16

First, 3-isobutyrylamino-5-propyl-2,4,6-trimethylaniline (10.0 g) and compound (A) (7.4 g) in the foregoing synthetic scheme were reacted in sulfolane (20 mL) in the presence of zinc chloride (4.1 g) by heating at 150° C. for 3 hours. The resulting solution was cooled and then added to 50 mL of 2 mol/L hydrochloric acid to precipitate crystals. The precipitated crystals was separated by filtration, washed with water, and dried. Then 6 g of the resulting dry product was added to 30 g of ice-cold concentrated sulfuric acid and then stirred at 20° C. to 25° C. for 4 hours. The reaction liquid was poured on 100 g of ice. The precipitated sulfonated product was separated by filtration and washed with cold water to give a precipitate. The resulting precipitate was suspended in 50 mL of water. The pH of the resulting suspension was adjusted to 7.0 with a 2 mol/L aqueous solution of sodium hydroxide to form a solution. Crystallization was performed with acetone to give exemplified compound 16 represented by a structural formula described below.

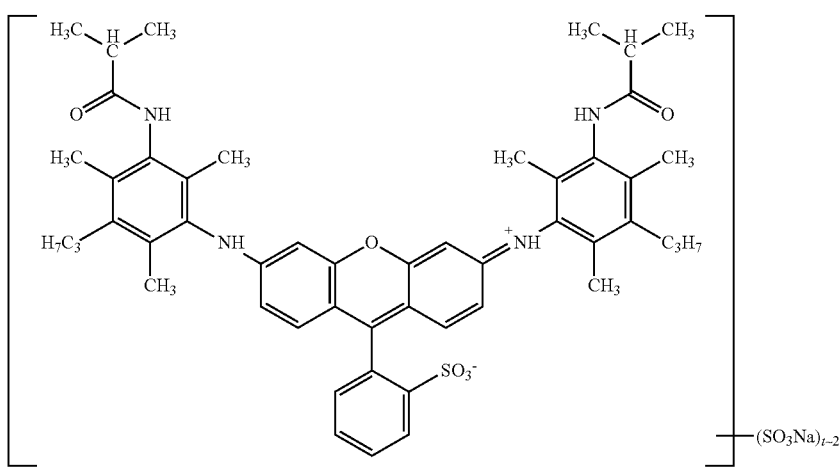

exemplified compound 16

The analysis of exemplified compound 16 by (1) $^1$H NMR analysis, (2) LC/TOF MS analysis and (3) UV/Vis spectral analysis demonstrated that exemplified compound 16 had the foregoing structure. The analytical results are described below.

Figure 4:
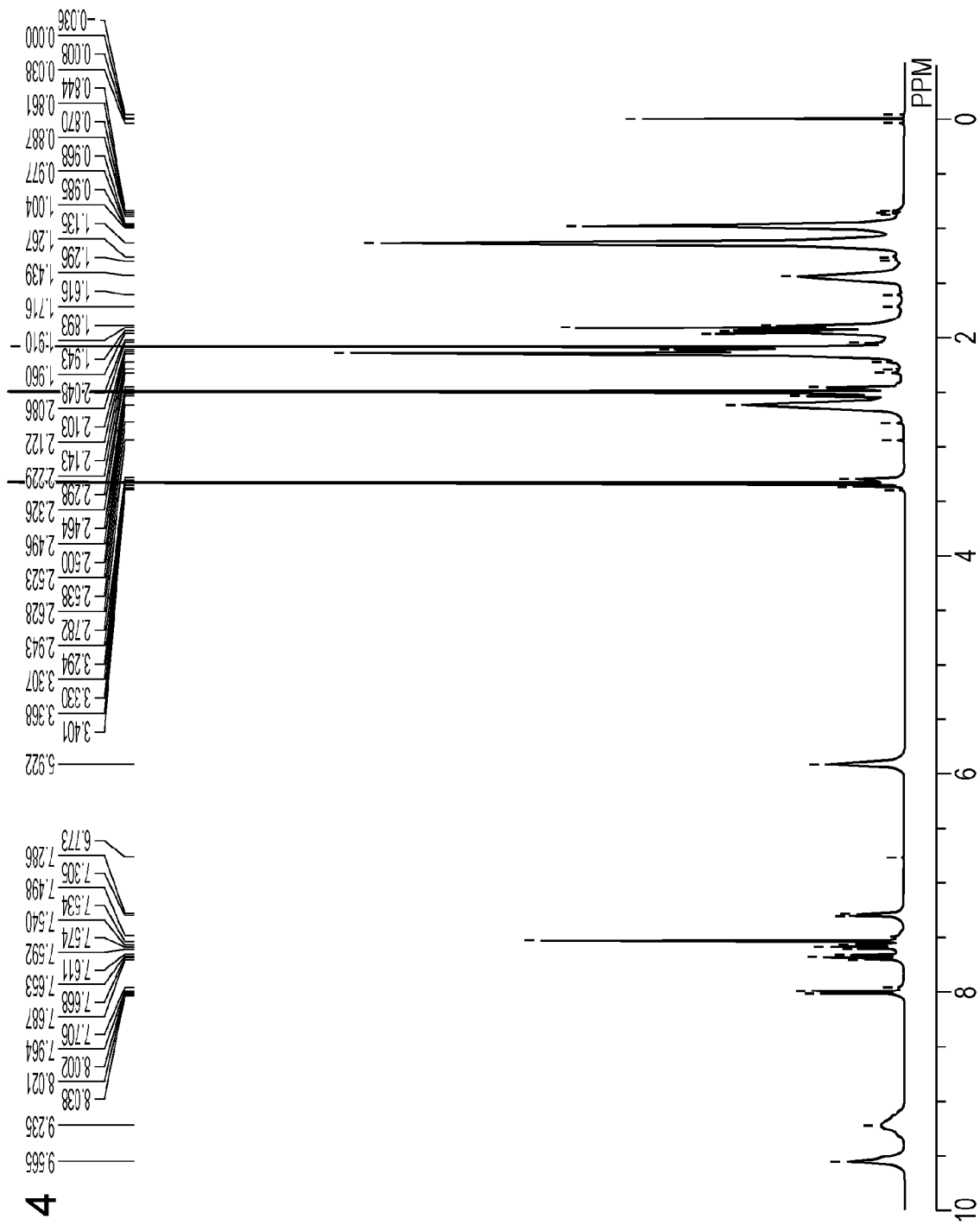
FIG. 4 is a chart illustrating the results of $^1$H NMR analysis of exemplified compound 16.

(1) Results of $^1$H NMR (400 MHz, DMSO-d$_6$, room temperature) (see FIG. 4):

δ [ppm]=9.57 (brs, 2H), 9.40-9.00 (br, 2H), 8.00 (d, 2H), 7.69 (t, 1H), 7.59 (t, 1H), 7.54 (s, 1H), 7.53 (s, 1H), 7.29 (d, 1H), 5.92 (s, 2H), 2.63 (s, 2H), 2.23-1.89 (m, 22H), 1.44 (brs, 4H), 1.30-0.83 (m, 18H);

(2) Results of LC/TOF MS analysis (eluent: 0.1% aqueous solution of acetic acid-methanol, ESI):

retention time: 14.0 minutes, purity=63.5% by area, m/z=1015.33 (n=2, [M-2Na+H]$^-$), retention time: 16.0 minutes, purity=35.9% by area, m/z=1015.33 (n=2, [M-2Na+H]$^-$);

(3) Results of UV/Vis spectral analysis (see FIG. 6):

$\lambda_{max}$=530 nm, ε=78923 M$^{-1}$ cm$^{-1}$ (in water, 25° C.)

Exemplified Compound 27

First, 3-isobutyrylamino-5-isobutyl-2,4,6-trimethylaniline (2.5 g) and compound (A) (7.4 g) in the foregoing synthetic scheme were reacted in sulfolane (20 mL) at 80° C. for 3 hours. Then 3-isobutyrylamino-5-propyl-2,4,6-trimethylaniline (7.5 g) was added thereto. The mixture was reacted in the presence of zinc chloride (4.1 g) by heating at 150° C. for 2 hours. The resulting solution was cooled and then added to 50 mL of 2 mol/L hydrochloric acid to precipitate crystals. The precipitated crystals was separated by filtration, washed with water, and dried. Then 6 g of the resulting dry product was added to 30 g of ice-cold concentrated sulfuric acid and then stirred at 20° C. to 25° C. for 4 hours. The reaction liquid was poured on 100 g of ice. The precipitated sulfonated product was separated by filtration and washed with cold water to give a precipitate. The resulting precipitate was suspended in 50 mL of water. The pH of the resulting suspension was adjusted to 7.0 with a 2 mol/L aqueous solution of sodium hydroxide to form a solution. Crystallization was performed with acetone to give exemplified compound 27 represented by a structural formula described below.

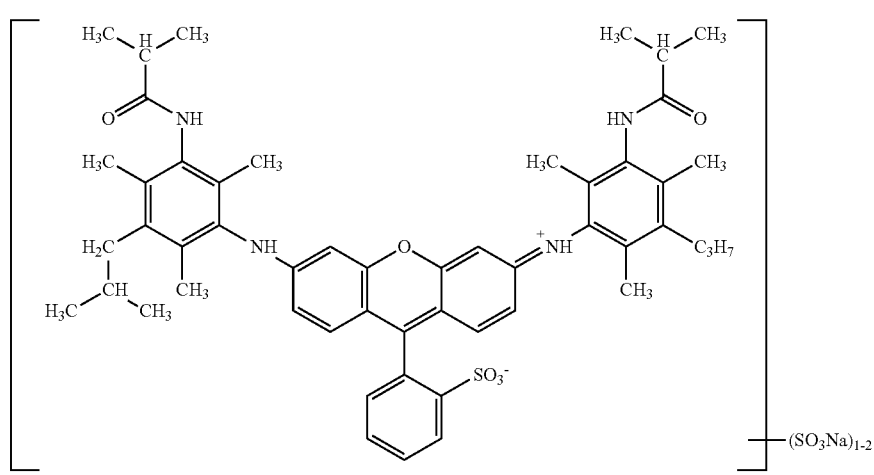

exemplified compound 27

The analysis of exemplified compound 27 by (1) $^1$H NMR analysis, (2) LC/TOF MS analysis and (3) UV/Vis spectral analysis demonstrated that exemplified compound 27 had the foregoing structure. The analytical results are described below.

Figure 5:
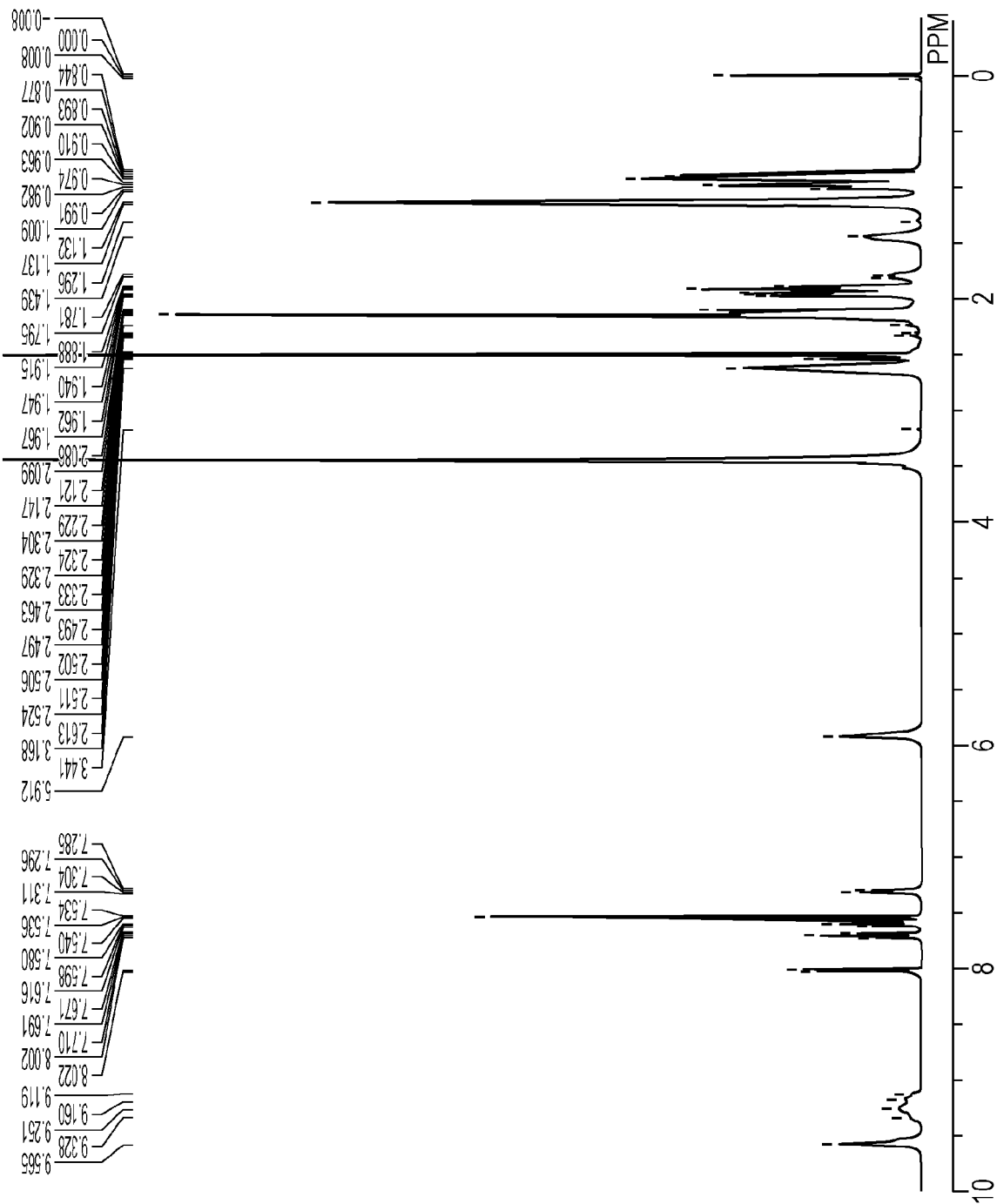
FIG. 5 is a chart illustrating the results of $^1$H NMR analysis of exemplified compound 27.

(1) Results of $^1$H NMR (400 MHz, DMSO-d$_6$, room temperature) (see FIG. 5):

δ [ppm]=9.57 (brs, 2H), 9.40-9.00 (br, 2H), 8.00 (d, 2H), 7.69 (t, 1H), 7.59 (t, 1H), 7.54 (s, 1H), 7.53 (s, 1H), 7.29 (d, 1H), 5.92 (s, 2H), 2.63 (s, 2H), 2.23-1.89 (m, 22H), 1.44 (brs, 4H), 1.30-0.83 (m, 18H);

(2) Results of LC/TOF MS analysis (eluent: 0.1% aqueous solution of acetic acid-methanol, ESI):

retention time: 14.0 minutes, purity=63.5% by area, m/z=1015.33 (n=2, [M-2Na+H]$^-$)

retention time: 16.0 minutes, purity=35.9% by area, m/z=1015.33 (n=2, [M-2Na+H]$^-$);

(3) Results of UV/Vis spectral analysis (see FIG. 6):

$\lambda_{max}$=535 nm, $\epsilon$=92783 M$^{-1}$ cm$^{-1}$ (in water, 25° C.)

Other Compounds

Compounds described in Table 1 were synthesized according to the foregoing synthetic methods. Structures of these compounds were identified in the same way as in exemplified compounds 1, 4, 15, 16 and 27. Table 1 also describes the structures of synthesized exemplified compounds 1, 4, 15, 16 and 27.

In Table 1, "Me" represents methyl, "Et" represents ethyl, "n-Pr" represents n-propyl, "i-Pr" represents i-propyl, "i-Bu" represents i-butyl, "t-Bu" represents tert-butyl, "1-MeBu" represents 1-methylbutyl, "n-Hx" represents n-hexyl and "Ph" represents phenyl. "*" represents the bonding site of a substituent.

TABLE 1

Exemplified compound represented by general formula.

| Exemplified compound | R$_1$ | R$_2$ | R$_3$ | R$_4$ | R$_5$ | R$_6$ | R$_7$ | R$_8$ | R$_9$ | R$_{10}$ | Z | n |
|---|---|---|---|---|---|---|---|---|---|---|---|---|
| 1 | Me | i-PrCONH | Me | Me | Me | Me | i-PrCONH | Me | Me | Me | SO$_3$Na | 1~2 |
| 2 | Me | i-PrCONH | Me | Et | Me | Me | i-PrCONH | Me | Et | Me | SO$_3$Na | 1~2 |
| 3 | Et | EtCONH | Et | Et | Et | Et | EtCONH | Et | Et | Et | SO$_3$Na | 1~2 |
| 4 | Me | i-PrCONH | Me | EtO | Me | Me | i-PrCONH | Me | EtO | Me | SO$_3$Na | 1~2 |
| 5 | Me | MeCONH | Me | n-Hx | Me | Me | MeCONH | Me | n-Hx | Me | SO$_3$Na | 1~2 |
| 6 | Me | i-PrCONH | Me | Me | Me | n-Pr | Me | n-Pr | H | Me | SO$_3$Na | 2~3 |
| 7 | Me | i-PrCONH | Me | n-Pr | Me | Me | i-PrCONH | Me | Me | Me | SO$_3$Na | 1~2 |
| 8 | Me | i-PrCONH | Me | i-Bu | Me | Me | MeCONH | H | 1-MeBu | Me | SO$_3$Na | 1~2 |
| 9 | n-Pr | MeCONH | H | Me | n-Pr | n-Pr | MeCONH | H | Me | n-Pr | SO$_3$Na | 1~2 |
| 10 | t-Bu | MeCONH | Me | Me | Me | t-Bu | MeCONH | Me | Me | Me | SO$_3$Na | 1~2 |
| 11 | Me | MeCONH | Me | MeCONH | Me | Me | MeCONH | Me | Me | Me | SO$_3$H | 1~2 |
| 12 | Me | i-PrCONH | Me | Me | Me | i-Pr | MeCONH | i-Pr | H | i-Pr | SO$_2$NH$_2$ | 1~2 |
| 13 | Me | 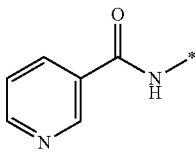 | Me | Me | Me | Me | 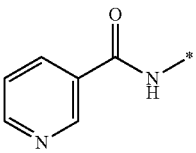 | Me | Me | Me | SO$_3$Na | 1~2 |
| 14 | Me | 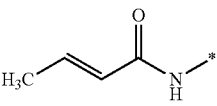 | Me | i-Pr | Me | Me | 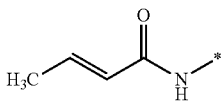 | Me | i-Pr | Me | SO$_3$Na | 1~2 |
| 15 | Me | i-PrCONH | Me | i-Bu | Me | Me | i-PrCONH | Me | i-Bu | Me | SO$_3$Na | 1~2 |
| 16 | Me | i-PrCONH | Me | n-Pr | Me | Me | i-PrCONH | Me | n-Pr | Me | SO$_3$Na | 1~2 |
| 17 | Me | PhCONH | Me | Me | Me | Me | PhCONH | Me | Me | Me | SO$_3$Na | 2~3 |
| 18 | Me | n-PrCONH | Me | n-PrO | Me | Me | n-PrCONH | Me | n-PrO | Me | SO$_3$Na | 1~2 |
| 19 | Me | MeCONH | Me | PhO | Me | Me | MeCONH | Me | PhO | Me | SO$_3$Na | 2~3 |
| 20 | Me | PhCONH | Me | Me | Me | Et | H | Me | H | Et | SO$_3$Na | 1~2 |
| 21 | Me | i-PrCONH | EtO | H | Me | Me | i-PrCONH | Me | n-Pr | Me | SO$_3$Na | 1~2 |
| 22 | Me | MeCONH | PhO | H | Me | Me | i-PrCONH | Me | Me | Me | SO$_3$NH$_4$ | 2~3 |
| 23 | n-Hx | MeCONH | Me | Me | Me | Me | MeCONH | Me | Me | Me | SO$_3$Li | 1~2 |
| 24 | Me | 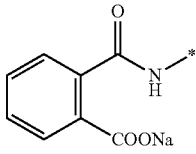 | Me | Me | Me | Me | 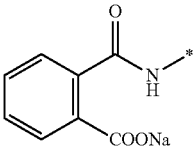 | Me | Me | Me | — | 0 |

TABLE 1-continued

Exemplified compound represented by general formula.

| Exemplified compound | $R_1$ | $R_2$ | $R_3$ | $R_4$ | $R_5$ | $R_6$ | $R_7$ | $R_8$ | $R_9$ | $R_{10}$ | Z | n |
|---|---|---|---|---|---|---|---|---|---|---|---|---|
| 25 | Me | cyclohexyl-C(O)NH- | Me | Et | Me | Me | cyclohexyl-C(O)NH- | Me | Et | Me | $SO_3K$ | 1~2 |
| 26 | Me | PhCH$_2$C(O)NH- | Me | t-Bu | Me | Me | PhCH$_2$C(O)NH- | Me | t-Bu | Me | $SO_3Na$ | 2~3 |
| 27 | Me | i-PrCONH | Me | i-Bu | Me | Me | i-PrCONH | Me | n-Pr | Me | $SO_3Na$ | 1~2 |
| 28 | Me | MeCONH | Me | i-Bu | Me | Me | MeCONH | Me | i-Bu | Me | $SO_3Na$ | 1~2 |

Preparation of Ink

Components described below (units: %) were mixed, and the mixture was sufficiently stirred to form a solution. The solution was subjected to the pressure-filtration with a filter having a pore size of 0.2 µm to prepare an ink. Tables 2 and 3 describe the contents $C_1$(%) of the compounds represented by the general formula (1) and the contents $C_2$(%) of the compounds having different structures from those of the compound represented by the general formula (1). Tables 2 and 3 also describe the values of the mass ratio (time) of "the content $C_1$ of the compound represented by the general formula (1)/the content $C_2$ of the compound having different structures from those represented by the general formula (1)".

Coloring material (a kind described in Tables 2 and 3): Amount used (%) described in Tables 2 and 3.

Ethylene glycol: 9.00%

Diethylene glycol: 9.00%

Acetylenol E100 (nonionic surfactant, manufactured by Kawaken Fine Chemicals Co., Ltd.): 1.00%

Deionized water: an amount such that the total amount was 100.00%.

Inks in Examples 5, 8, 11, 12 and 24 were required to be heated in their preparations because the coloring materials had low solubility. Inks in other examples and comparative examples were prepared at ordinary temperature (25° C.).

TABLE 2

Composition and properties of ink.

| | | Composition of ink | | | Properties of ink | | |
|---|---|---|---|---|---|---|---|
| | Compound represented by general formula (1) | Amount used (%) | Other coloring materials | Amount used (%) | Content $C_1$ (%) | Content $C_2$ (%) | Mass ratio $C_1/C_2$ (time) |
| Example 1 | exemplified compound 1 | 3.50 | — | — | 3.50 | 0.00 | — |
| 2 | exemplified compound 2 | 3.50 | — | — | 3.50 | 0.00 | — |
| 3 | exemplified compound 3 | 3.50 | — | — | 3.50 | 0.00 | — |
| 4 | exemplified compound 4 | 3.50 | — | — | 3.50 | 0.00 | — |
| 5 | exemplified compound 5 | 3.50 | — | — | 3.50 | 0.00 | — |
| 6 | exemplified compound 6 | 3.50 | — | — | 3.50 | 0.00 | — |
| 7 | exemplified compound 7 | 3.50 | — | — | 3.50 | 0.00 | — |
| 8 | exemplified compound 8 | 3.50 | — | — | 3.50 | 0.00 | — |
| 9 | exemplified compound 9 | 3.50 | — | — | 3.50 | 0.00 | — |
| 10 | exemplified compound 10 | 3.50 | — | — | 3.50 | 0.00 | — |
| 11 | exemplified compound 11 | 3.50 | — | — | 3.50 | 0.00 | — |
| 12 | exemplified compound 12 | 3.50 | — | — | 3.50 | 0.00 | — |
| 13 | exemplified compound 13 | 3.50 | — | — | 3.50 | 0.00 | — |
| 14 | exemplified compound 14 | 3.50 | — | — | 3.50 | 0.00 | — |
| 15 | exemplified compound 15 | 3.50 | — | — | 3.50 | 0.00 | — |
| 16 | exemplified compound 16 | 3.50 | — | — | 3.50 | 0.00 | — |
| 17 | exemplified compound 17 | 3.50 | — | — | 3.50 | 0.00 | — |
| 18 | exemplified compound 18 | 3.50 | — | — | 3.50 | 0.00 | — |
| 19 | exemplified compound 19 | 3.50 | — | — | 3.50 | 0.00 | — |
| 20 | exemplified compound 20 | 3.50 | — | — | 3.50 | 0.00 | — |

TABLE 2-continued

Composition and properties of ink.

| | Composition of ink | | | | Properties of ink | | |
|---|---|---|---|---|---|---|---|
| | Compound represented by general formula (1) | Amount used (%) | Other coloring materials | Amount used (%) | Content $C_1$ (%) | Content $C_2$ (%) | Mass ratio $C_1/C_2$ (time) |
| 21 | exemplified compound 21 | 3.50 | — | — | 3.50 | 0.00 | — |
| 22 | exemplified compound 22 | 3.50 | — | — | 3.50 | 0.00 | — |
| 23 | exemplified compound 23 | 3.50 | — | — | 3.50 | 0.00 | — |
| 24 | exemplified compound 24 | 3.50 | — | — | 3.50 | 0.00 | — |
| 25 | exemplified compound 25 | 3.50 | — | — | 3.50 | 0.00 | — |
| 26 | exemplified compound 26 | 3.50 | — | — | 3.50 | 0.00 | — |
| 27 | exemplified compound 27 | 3.50 | — | — | 3.50 | 0.00 | — |
| 28 | exemplified compound 28 | 3.50 | — | — | 3.50 | 0.00 | — |
| 29 | exemplified compound 15<br>exemplified compound 16 | 1.75<br>1.75 | — | — | 3.50 | 0.00 | — |
| 30 | exemplified compound 16 | 1.00 | azo compound 1 | 2.50 | 1.00 | 2.50 | 0.40 |
| 31 | exemplified compound 16 | 1.00 | azo compound 2 | 2.50 | 1.00 | 2.50 | 0.40 |
| 32 | exemplified compound 16 | 1.00 | anthrapyridone compound 1 | 2.50 | 1.00 | 2.50 | 0.40 |

TABLE 3

Composition and properties of ink.

| | | Composition of ink | | | | Properties of ink | | |
|---|---|---|---|---|---|---|---|---|
| | | Compound represented by general formula (1) | Amount used (%) | Other coloring material | Amount used (%) | Content $C_1$ (%) | Content $C_2$ (%) | Mass ratio $C_1/C_2$ (time) |
| Example | 33 | exemplified compound 16 | 1.00 | anthrapyridone compound 2 | 2.50 | 1.00 | 2.50 | 0.40 |
| | 34 | exemplified compound 16 | 1.00 | azo compound 1<br>anthrapyridone compound 1 | 1.25<br>1.25 | 1.00 | 2.50 | 0.40 |
| | 35 | exemplified compound 16 | 1.00 | azo compound 2<br>anthrapyridone compound 2 | 1.25<br>1.25 | 1.00 | 2.50 | 0.40 |
| | 36 | exemplified compound 1 | 1.00 | azo compound 1 | 2.50 | 1.00 | 2.50 | 0.40 |
| | 37 | exemplified compound 4 | 1.00 | azo compound 1 | 2.50 | 1.00 | 2.50 | 0.40 |
| | 38 | exemplified compound 9 | 1.00 | azo compound 1 | 2.50 | 1.00 | 2.50 | 0.40 |
| | 39 | exemplified compound 10 | 1.00 | azo compound 1 | 2.50 | 1.00 | 2.50 | 0.40 |
| | 40 | exemplified compound 15 | 1.00 | azo compound 1 | 2.50 | 1.00 | 2.50 | 0.40 |
| | 41 | exemplified compound 20 | 1.00 | azo compound 1 | 2.50 | 1.00 | 2.50 | 0.40 |
| | 42 | exemplified compound 24 | 1.00 | azo compound 1 | 2.50 | 1.00 | 2.50 | 0.40 |
| | 43 | exemplified compound 25 | 1.00 | azo compound 1 | 2.50 | 1.00 | 2.50 | 0.40 |
| | 44 | exemplified compound 27 | 1.00 | azo compound 1 | 2.50 | 1.00 | 2.50 | 0.40 |
| | 45 | exemplified compound 28 | 1.00 | azo compound 1 | 2.50 | 1.00 | 2.50 | 0.40 |
| | 46 | exemplified compound 16 | 3.20 | azo compound 1 | 0.30 | 3.20 | 0.30 | 10.67 |
| | 47 | exemplified compound 16 | 3.15 | azo compound 1 | 0.35 | 3.15 | 0.35 | 9.00 |
| | 48 | exemplified compound 16 | 2.80 | azo compound 1 | 0.70 | 2.80 | 0.70 | 4.00 |
| | 49 | exemplified compound 16 | 1.80 | azo compound 1 | 1.70 | 1.80 | 1.70 | 1.06 |
| | 50 | exemplified compound 16 | 1.75 | azo compound 1 | 1.75 | 1.75 | 1.75 | 1.00 |
| | 51 | exemplified compound 28 | 1.75 | azo compound 1 | 1.75 | 1.75 | 1.75 | 1.00 |
| | 52 | exemplified compound 16 | 0.35 | azo compound 1 | 3.15 | 0.35 | 3.15 | 0.11 |
| | 53 | exemplified compound 16 | 0.30 | azo compound 1 | 3.20 | 0.30 | 3.20 | 0.09 |
| Comparative Example | 1 | — | — | comparative compound 1 | 3.50 | 0.00 | 3.50 | 0.00 |
| | 2 | — | — | comparative compound 2 | 3.50 | 0.00 | 3.50 | 0.00 |
| | 3 | — | — | comparative compound 3 | 3.50 | 0.00 | 3.50 | 0.00 |
| | 4 | — | — | comparative compound 4 | 3.50 | 0.00 | 3.50 | 0.00 |
| | 5 | — | — | comparative compound 5 | 3.50 | 0.00 | 3.50 | 0.00 |
| | 6 | — | — | azo compound 1 | 3.50 | 0.00 | 3.50 | 0.00 |
| | 7 | — | — | azo compound 2 | 3.50 | 0.00 | 3.50 | 0.00 |
| | 8 | — | — | anthrapyridone compound 1 | 3.50 | 0.00 | 3.50 | 0.00 |
| | 9 | — | — | anthrapyridone compound 2 | 3.50 | 0.00 | 3.50 | 0.00 |
| | 10 | — | — | comparative compound 1<br>azo compound 1 | 1.00<br>2.50 | 0.00 | 3.50 | 0.00 |
| | 11 | — | — | comparative compound 5<br>azo compound 1 | 1.00<br>2.50 | 0.00 | 3.50 | 0.00 |

Azo compound 1 was used as a lithium salt, and azo compound 2 and anthrapyridone compounds 1 and 2 were used as sodium salts, these compounds having the foregoing structures. The structures of comparative compounds 1 to 5 are illustrated below. Comparative compound 1 is C.I. Acid Red 289. Comparative compound 2 is C.I. Acid Red 52.

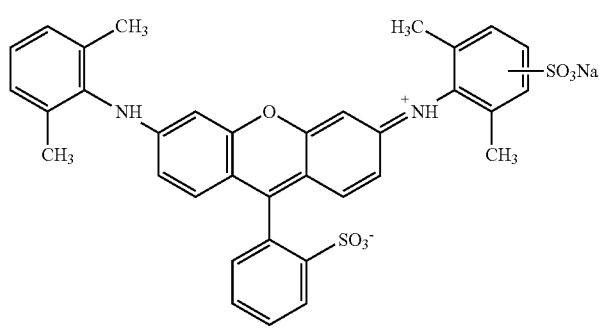
comparative compound 1
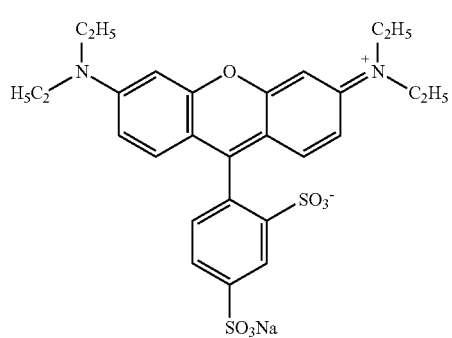
comparative compound 2
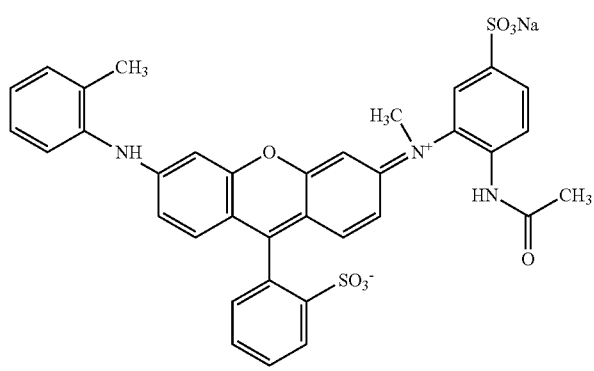
comparative compound 3
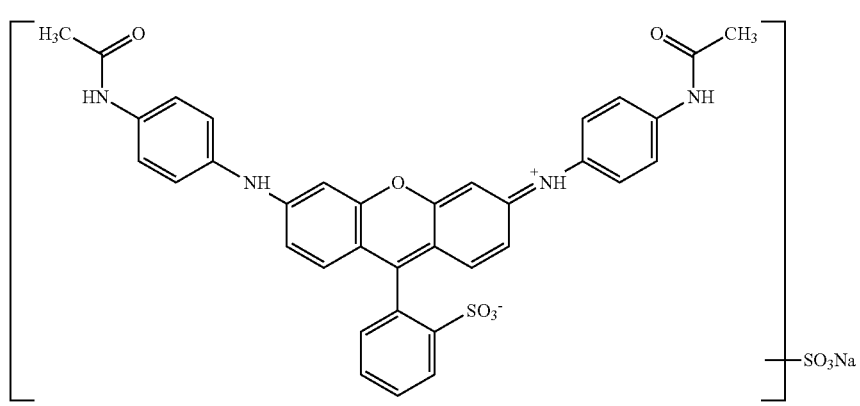
comparative compound 4

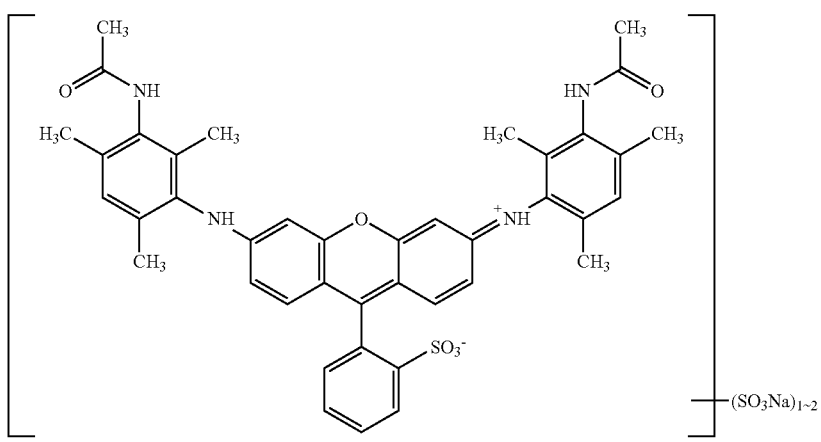

comparative compound 5

Evaluation

Evaluations as described below were made on exemplified compounds 1, 4, 15, 16 and 27 and the inks. Colors of images were measured with a spectrophotometer (trade name: Spectrolino, manufactured by GretagMacbeth AG) using a D50 light source at a visual field of 2°. L*, a* and b* are those in the L*a*b* color space specified by Commission Internationale de l'Eclairage (CIE).

Properties of Compound Represented by General Formula (1)

To compare the properties of the compounds represented by the general formula (1) with the properties of coloring materials having xanthene skeletons in the related art, evaluations as described below were performed. Specifically, C.I. Acid Red 289 and C.I. Acid Red 52 were analyzed under the same conditions (in water, 25° C.) as in (3) UV/Vis spectral analysis among the foregoing identification methods. As is clear from FIG. 6, each of exemplified compounds 1, 4, 15, 16 and 27, which were typical compounds represented by the general formula (1), had a maximum absorption wavelength $\lambda_{max}$ of about 530 nm and a preferable magenta hue. Furthermore, they each had high absorbance at $\lambda_{max}$ and excellent color developability. In contrast, while C.I. Acid Red 289 had a preferable hue close to magenta, C.I. Acid Red 289 had low absorbance at $\lambda_{max}$ and relatively low color developability. While C.I. Acid Red 52 had high absorbance at $\lambda_{max}$ to some extent and good color developability, C.I. Acid Red 52 had a bluish magenta hue, which was less preferred.

Color Developability

Each of the inks prepared as described above was filled into an ink cartridge. The cartridge was mounted on an ink jet recording apparatus (PIXUS iP8600, manufactured by CANON KABUSHIKI KAISHA) configured to eject the ink from a recording head by the effect of thermal energy. In the present examples, a solid image recorded by applying 8 ink droplets (2.5 pL per droplet) to an unit area of 1/600 inch×1/600 inch is defined as a solid image having a recording duty of 100%. Ten types of solid images having different recording duties from 10% to 100% in 10% steps were recorded on plain paper (PB PAPER, manufactured by CANON KABUSHIKI KAISHA) with the ink jet recording apparatus in an environment with a temperature of 23° C. and a relative humidity of 55% to form a recorded article. The resulting recorded article was dried for 24 hours in an environment with a temperature of 23° C. and a relative humidity of 55%.

In portions of the solid images of the recorded article, a* and b* were measured for each recording duty. The chroma was calculated from the expression $C^*=\{(a^*)^2+(b^*)^2\}^{1/2}$ using the values of a* and b* of the solid image having a recording duty of 100%. Among the 10 types of solid images, a solid image having a* closest to 50 was determined, and the hue angle H° was calculated from the following expressions using the values of a* and b* of the solid image:

Hue angle $H°=\tan^{-1}(b^*/a^*)$ when $a^*≥0$ and $b^*≥0$ (first quadrant),

Hue angle $H°=180+\tan^{-1}(b^*/a^*)$ when $a^*≤0$ and $b^*≥0$ (second quadrant), Hue angle $H°=180+\tan^{-1}(b^*/a^*)$ when $a^*≤0$ and $b^*≤0$ (third quadrant), and Hue angle $H°=360+\tan^{-1}(b^*/a^*)$ when $a^*≥0$ and $b^*≤0$ (fourth quadrant).

The color developability was evaluated according to the following evaluation criteria using the values of C* and H°:

A: H° was 340 or more and less than 360, and C* was 65 or more.
B: H° was 340 or more and less than 360, and C* was 63 or more and less than 65.
C: H° was 0 or more and less than 340, or C* was less than 63.

In examples of the present invention, the color developability levels rated as A and B were defined as acceptable levels. The color developability level rated as C was defined as unacceptable level. Table 4 describes the evaluation results.

Light fastness: conditions 1 and 2

Solid images each having a recording duty of 100% were recorded to form recorded articles with the same recording apparatus and conditions as above, except that glossy paper (CANON Photo Paper Pro Platinum PT-101, manufactured by CANON KABUSHIKI KAISHA) was used as a recording medium. The resulting recorded articles were dried for 24 hours in an environment with a temperature of 23° C. and a relative humidity of 55%. The optical density of the solid image of each of the recorded articles was measured (hereinafter, referred to as an "optical density before testing"). Then the recorded articles were placed in a xenon tester (Xenon Weather Meter SX-75, manufactured by Suga Test Instruments Co., Ltd.) and irradiated with xenon light at a temperature in a chamber of 23° C., a relative humidity of 50% and an illuminance of 50 klx for 240 hours (condition 1) and 360 hours (condition 2). The optical density of the solid image of each of the recorded articles was measured (hereinafter, referred to as an "optical density after testing"). Then the residual rate of the optical density (%) was calculated from the expression: Residual rate of optical density (%)=(optical density after testing/optical density before testing)×100. The light fastness (under the conditions 1 and 2) was evaluated according to the following evaluation criteria for each article.

Evaluation Criteria for Condition 1

A: The residual rate of the optical density was 85% or more.
B: The residual rate of the optical density was 75% or more and less than 85%.
C: The residual rate of the optical density was 65% or more and less than 75%.
D: The residual rate of the optical density was less than 65%.

According to examples of the present invention, the levels of the residual rates rated as A and B under condition 1 were defined as acceptable levels. The levels of the residual rates rated as C and D under condition 1 were defined as unacceptable levels. Table 4 describes the evaluation results.

Evaluation Criteria for Condition 2

AA: The residual rate of the optical density was 90% or more.
A: The residual rate of the optical density was 85% or more and less than 90%.
B: The residual rate of the optical density was 75% or more and less than 85%.
C: The residual rate of the optical density was less than 75%.

Under condition 2, the light fastness of the images was evaluated under stricter conditions than condition 1. The ranks C, B, A and AA are arranged in the order of their increasing light fastness. Table 4 describes the evaluation results.

Moisture Resistance

Images each having a pattern described below were recorded to form recorded articles with the same recording apparatus and conditions as above, except that glossy paper (CANON Photo Paper Glossy Gold GL-101, manufactured by CANON KABUSHIKI KAISHA) was used as a recording medium. The pattern was one in which solid images each having a recording duty of 100% and non-recorded portions each having the same size as the solid image were arranged in a grid-like shape. The resulting recorded articles were dried for 24 hours in an environment with a temperature of 23° C. and a relative humidity of 55%. L*, a* and b* of portions of the solid images of each of the recorded articles were measured (hereinafter, referred to as "$L_1^*$", "$a_1^*$" and "$b_1^*$", respectively). The recorded articles were placed in a thermo-hygrostat set at a temperature of 30° C. and a relative humidity of 90% for 168 hours. L*, a* and b* of the portions of the solid images of each of the recorded articles were measured (hereinafter, referred to as "$L_2^*$", "$a_2^*$" and "$b_2^*$", respectively). A color change (δE) was calculated from Color change $(\delta E)=\{(L_1^*-L_2^*)(a_1^*-a_2^*)2+(b_1^*-b_2^*)^2\}^{1/2}$. The moisture resistance was evaluated according to evaluation criteria described below:

A: δE was less than 5.
B: δE was 5 or more and less than 10.
C: δE was 10 or more and less than 15.
D: δE was 15 or more.

According to examples of the present invention, the moisture resistance levels rated as A and B were defined as acceptable levels. The moisture resistance levels rated as C and D were defined as unacceptable levels. Table 4 described the evaluation results.

TABLE 4

Evaluation results.

|  |  | Color developability | Moisture resistance | Light fastness (1) | Light fastness (2) |
|---|---|---|---|---|---|
| Example | 1 | A | A | A | C |
|  | 2 | A | A | A | C |
|  | 3 | A | A | A | C |
|  | 4 | A | A | A | C |
|  | 5 | A | A | A | C |
|  | 6 | A | A | A | C |
|  | 7 | A | A | A | C |
|  | 8 | A | B | A | C |
|  | 9 | A | B | A | C |
|  | 10 | A | A | B | C |
|  | 11 | A | B | A | C |
|  | 12 | A | B | A | C |
|  | 13 | B | B | B | C |
|  | 14 | B | B | B | C |
|  | 15 | A | A | A | C |
|  | 16 | A | A | A | C |
|  | 17 | A | A | A | C |
|  | 18 | A | A | A | C |
|  | 19 | A | B | A | C |
|  | 20 | A | B | A | C |
|  | 21 | A | B | A | C |
|  | 22 | A | B | A | C |
|  | 23 | A | A | B | C |
|  | 24 | A | B | A | C |
|  | 25 | A | B | B | C |
|  | 26 | A | B | B | C |
|  | 27 | A | A | A | C |
|  | 28 | A | A | A | C |
|  | 29 | A | A | A | C |
|  | 30 | A | A | A | AA |
|  | 31 | A | A | A | AA |
|  | 32 | A | A | A | AA |
|  | 33 | A | A | A | AA |
|  | 34 | A | A | A | AA |
|  | 35 | A | A | A | AA |
|  | 36 | A | A | A | AA |
|  | 37 | A | A | A | AA |
|  | 38 | A | B | A | AA |
|  | 39 | A | A | A | AA |
|  | 40 | A | A | A | AA |
|  | 41 | A | B | A | AA |
|  | 42 | A | B | A | AA |
|  | 43 | A | B | A | AA |
|  | 44 | A | A | A | AA |
|  | 45 | A | A | A | AA |
|  | 46 | A | A | A | B |
|  | 47 | A | A | A | A |
|  | 48 | A | A | A | A |
|  | 49 | A | A | A | A |
|  | 50 | A | A | A | AA |
|  | 51 | A | A | A | AA |
|  | 52 | A | A | A | AA |
|  | 53 | A | A | A | AA |
| Comparative example | 1 | A | D | D | C |
|  | 2 | C | D | C | C |
|  | 3 | A | C | C | C |
|  | 4 | C | C | C | C |
|  | 5 | A | C | A | C |
|  | 6 | C | A | A | AA |
|  | 7 | A | C | A | B |
|  | 8 | C | D | A | AA |
|  | 9 | C | A | A | AA |
|  | 10 | A | D | C | C |
|  | 11 | A | C | A | B |

The color developability in Example 53 was rated as rank A. However, Example 53 was relatively inferior to Example 52.

As described above, the compound represented by the general formula (1) according to an embodiment of the present invention has a magenta hue similar to that of C.I. Acid Red 289 and excellent color developability. Furthermore, the compound represented by the general formula (1) overcomes the drawbacks of C.I. Acid Red 289 and has excellent levels of light fastness and moisture resistance. Moreover, the combination use of the compound represented by the general formula (1) and a coloring material having a different structure from that of the compound represented by the general formula (1) results in further improvement in light fastness.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-057563 filed Mar. 21, 2013, which is hereby incorporated by reference herein in its entirety.

What is claimed is:

1. A compound represented by the following general formula (1):

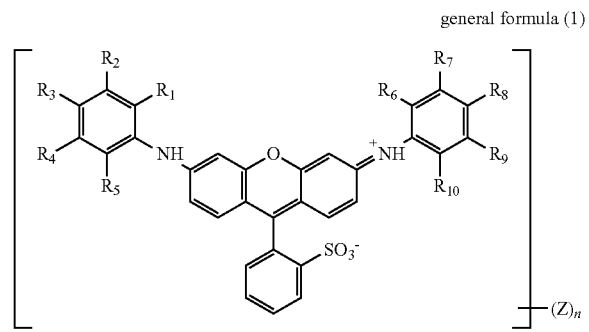

general formula (1)

wherein $R_1$, $R_5$, $R_6$ and $R_{10}$ each independently represent an alkyl group; $R_3$ and $R_8$ each independently represent a hydrogen atom, an alkyl group, an alkoxy group or an aryloxy group; $R_2$, $R_4$, $R_7$ and $R_9$ each independently represent a hydrogen atom, an alkyl group, an alkoxy group, an aryloxy group or a group represented by the general formula (2) described below, at least one of $R_2$, $R_4$, $R_7$ and $R_9$ represents an alkyl group, an alkoxy group or an aryloxy group, and at least one of $R_2$, $R_4$, $R_7$ and $R_9$ represents a group represented by general formula (2) described below; Z independently represents a sulfonic group or a sulfamoyl group; n represents an integer of 0 to 3 when at least one of $R_2$, $R_3$, $R_4$, $R_7$, $R_8$ and $R_9$ contains an ionic group, and n represents an integer of 1 to 3 when none of $R_2$, $R_3$, $R_4$, $R_2$, $R_8$ and $R_9$ contains an ionic group; and when Z is present, Z is substituted for at least one hydrogen atom of an aromatic ring in the general formula (1),

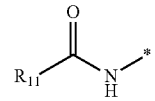

general formula (2)

wherein $R_{11}$ represents an alkyl group, a cycloalkyl group, an aryl group, an aralkyl group, an alkenyl group or a heterocyclic group; and * represents the bonding site of an aromatic ring in the general formula (1).

2. The compound according to claim 1, wherein $R_{11}$ in the general formula (2) represents an alkyl group or an aryl group.

3. The compound according to claim 1, wherein in the general formula (1), n represents an integer of 1 to 3, and
Z represents a sulfonic group in the form of a salt.

4. The compound according to claim 1, wherein in the general formula (1), $R_1$, $R_5$, $R_6$ and $R_{10}$ each independently represent an alkyl group having 1 to 3 carbon atoms.

5. The compound according to claim 1, wherein in the general formula (1), $R_3$ and $R_8$ each independently represent an alkyl group having 1 to 3 carbon atoms.

6. The compound according to claim 1, wherein in the general formula (1), $R_1$ and $R_6$ represent the same group,
$R_2$ and $R_7$ represent the same group,
$R_3$ and $R_8$ represent the same group,
$R_4$ and $R_9$ represent the same group, and
$R_5$ and $R_{10}$ represent the same group.

7. The compound according to claim 1, wherein in the general formula (1), $R_2$ and $R_7$ each represent a group represented by the general formula (2), and $R_4$ and $R_9$ each represent an alkyl group.

8. An ink comprising:
a coloring material,
wherein the coloring material contains a compound represented by the following general formula (1):

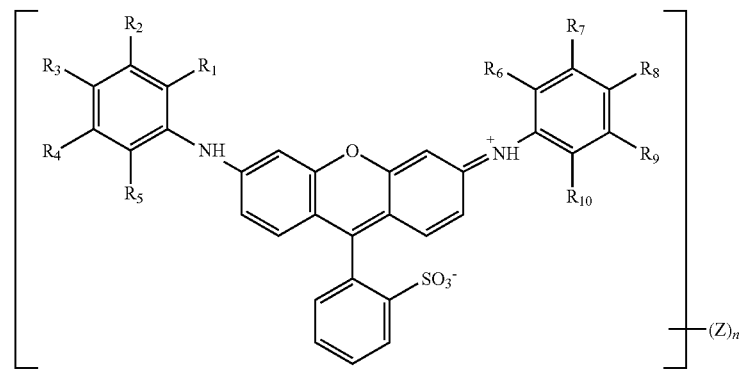

general formula (1)

wherein $R_1$, $R_5$, $R_6$ and $R_{10}$ each independently represent an alkyl group; $R_3$ and $R_8$ each independently represent a hydrogen atom, an alkyl group, an alkoxy group or an aryloxy group; $R_2$, $R_4$, $R_7$ and $R_9$ each independently represent a hydrogen atom, an alkyl group, an alkoxy group, an aryloxy group or a group represented by the general formula (2) described below, at least one of $R_2$, $R_4$, $R_7$ and $R_9$ represents an alkyl group, an alkoxy group or an aryloxy group, and at least one of $R_2$, $R_4$, $R_7$ and $R_9$ represents a group represented by general formula (2) described below; Z independently represents a sulfonic group or a sulfamoyl group; n represents an integer of 0 to 3 when at least one of $R_2$, $R_3$, $R_4$, $R_7$, $R_8$ and $R_9$ contains an ionic group, and n represents an integer of 1 to 3 when none of $R_2$, $R_3$, $R_4$, $R_7$, $R_8$ and $R_9$ contains an ionic group; and when Z is present, Z is substituted for at least one hydrogen atom of an aromatic ring in the general formula (1), general formula (2)

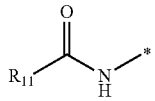

wherein $R_{11}$ represents an alkyl group, a cycloalkyl group, an aryl group, an aralkyl group, an alkenyl group or a heterocyclic group; and * represents the bonding site of an aromatic ring in the general formula (1).

9. The ink according to claim 8, wherein the coloring material further contains a compound having a different structure from that of the compound represented by the general formula (1).

10. The ink according to claim 8, wherein the ink is an ink jet ink.

11. An ink cartridge comprising:

an ink; and an ink storage portion, wherein the ink comprises the ink according to claim 8.

12. An ink jet recording method comprising ejecting an ink from a recording head of an ink jet system to record an image on a recording medium, wherein the ink comprises the ink according to claim 8.

* * * * *